United States Patent
Moini et al.

(10) Patent No.: US 6,863,790 B1
(45) Date of Patent: Mar. 8, 2005

(54) SHEATHLESS INTERFACE FOR CAPILLARY ELECTROPHORESIS/ELECTROSPRAY IONIZATION-MASS SPECTROMETRY USING AN IN-CAPILLARY ELECTRODE

(75) Inventors: Mehdi Moini, Austin, TX (US); Ping Cao, San Mateo, CA (US)

(73) Assignee: Board of Regents University of Texas System, Austin, TX (US)

( * ) Notice: Subject to any disclaimer, the term of this patent is extended or adjusted under 35 U.S.C. 154(b) by 0 days.

(21) Appl. No.: 09/370,781

(22) Filed: Aug. 5, 1999

Related U.S. Application Data

(63) Continuation of application No. PCT/US98/02118, filed on Feb. 5, 1998.
(60) Provisional application No. 60/036,922, filed on Feb. 6, 1997.

(51) Int. Cl.$^7$ ........................ G01N 27/447; G01N 30/72
(52) U.S. Cl. ........................ 204/452; 204/454; 204/603; 250/288
(58) Field of Search ........................ 250/288; 204/452, 204/603, 451, 453, 454, 455, 601, 602, 604, 605

(56) References Cited

U.S. PATENT DOCUMENTS

| | | | | | |
|---|---|---|---|---|---|
| 4,838,999 | A | * | 6/1989 | Haar et al. | 204/409 |
| 5,482,608 | A | * | 1/1996 | Keely et al. | 204/299 |
| 5,525,197 | A | * | 6/1996 | Coulson | 204/409 |
| 5,607,646 | A | * | 3/1997 | Okano et al. | 422/100 |
| 5,650,058 | A | * | 7/1997 | Wenske et al. | 205/615 |
| 5,993,633 | A | * | 11/1999 | Smith et al. | 204/601 |

OTHER PUBLICATIONS

P.W. Atkins, "Physical Chemistry", 4th Edition, 1990, pp. 147–151.*

* cited by examiner

*Primary Examiner*—Robert J. Warden, Sr.
*Assistant Examiner*—Kaj K. Olsen
(74) *Attorney, Agent, or Firm*—Fulbright & Jaworski, LLP

(57) ABSTRACT

A simple and rugged sheathless interface for capillary electrophoresis/electrospray ionization-mass spectrometry (CE/ESI-MS) was designed using common laboratory tools and chemicals. The interface uses a small platinum (Pt) wire which is inserted into the CE capillary through a small hole near the terminus. The position of the wire inside the CE capillary and within the buffer solution is analogous to standard CE separation operations where the terminus of the CE capillary is placed inside a buffer reservoir along with a grounded platinum electrode. By combining the use of the in-capillary electrode interface with sharpening of the fused silica tip of the CE capillary outlet, a stable electrospray current was maintained for an extended period of time. The design was successfully applied to CE/ESI-MS separations and analysis of mixtures of peptides and proteins. A detection limit of approximately 4 femtomole (S/N=3) was achieved for detection of myoglobin utilizing a 75 μm-i.d. aminopropylsilane treated CE column and using a wide scan range of 550–1350 Da. The advantages of this new design include: (1) a stable CE and ESI current, (2) durability, (3) a reduced risk of sparking between the capillary tip and the inlet of the mass spectrometer, (4) lack of any dead volume, and (5) facile fabrication with common tools and chemicals.

8 Claims, 22 Drawing Sheets

SHEATHLESS INTERFACE FOR CAPILLARY ELECTROPHORESIS/ ELECTROSPRAY IONIZATION-MASS SPECTROMETRY USING AN IN-CAPILLARY ELECTRODE

This is a continuation of co-pending application Ser. No. PCT/US98/02118, international filing date Feb. 5, 1998, which claims priority to U.S. Provisional Patent Application No. 60/036,922 filed Feb. 6, 1997.

1.0 BACKGROUND OF THE INVENTION

1.1 Field of the Invention

The present invention relates generally to a new process for the interfacing of capillary electrophoresis to mass spectrometry via electrospray ionization. More particularly, it concerns a novel sheathless interface useful for capillary electrophoresis/electrospray ionization.

1.2 Description of Related Art

The combination of mass spectrometry (MS) with a high-efficiency separation technique such as capillary electrophoresis (CE) provides a powerful system for the analysis of complex biological mixtures (William 1996). Currently, electrospray ionization (ESI) serves as the most common interface between CE and MS. A particularly important feature of any CE-MS interface is the method used to establish and maintain the electrical connection at the CE capillary terminus. These connections serve to close the CE electrical circuit and to provide a connection for the ESI voltage. The methods used to maintain these connections can be divided in two general categories: sheath-flow interfaces and sheathless interfaces. Comprehensive reviews of current CE/ESI-MS interfaces have been described by Cai et al. (Cai and Henion 1995) and Severs et al. (Severs, et al. 1996).

The sheath-flow configuration has been the most widely used interface for CE/ESI-MS, especially in commercial instrumentation. Sheathed techniques include Smith and co-workers' coaxial system (Smith et al. 1988) and the liquid junction technique established by Lee and co-workers (Lee et al. 1989). Sheath-flow configurations have several advantages including simple fabrication, reliability, and case of implementation. However, these techniques also bear several disadvantages: (1) dilution of the analyte by the sheath liquid; (2) competition for available charge between the species present in the sheath-flow and the analyte in the ESI process (Gale and Smith 1993); and (3) effects on separation, solubility, or molecular conformation which vary according to sheath liquid composition (Thompson et al. 1993, Foret et al. 1994, Smith et al. 1991).

In an attempt to remedy these problems, Severs et al. (1996) recently developed a new CE/ESI-MS interface in which the terminus of the CE separation capillary and a short ESI emitter capillary are connected by polysulphone microdialysis tubing. The electrical connection is provided outside the membrane via an electrode in a small sheath liquid reservoir that serves to close the CE circuit and simultaneously establish the electrospray voltage.

The first successful sheathless coupling of CE with MS was reported by Olivares et al. (1987). In this initial work, the outlet of the CE capillary was terminated within a stainless steel capillary which functioned as both a CE electrode and the electrospray needle. In this configuration, however, there was a relatively large dead volume at the capillary terminus. The current version of the sheathless source uses a gold conductive coating at the CE Wahl and Smith (1994) presented a somewhat similar CE-MS interfacing approach, however, the electrical connection to the end of separation capillary was made though a micro-hole 2 cm from the end of the CE column. The micro-hole was sealed by conductive gold epoxy, through which electrical contact was made. Results presented by the inventors' laboratory (Cao and Moini 1995) and others show that these types of designs increase sensitivity by avoiding dilution of the sample with the sheath liquid. However, the CE capillaries made with the conductive gold tip or with the conductive gold epoxy have a short lifetime due to degradation of the gold tip or conductive gold contact as a result of chemical, electrochemical, and/or electrical phenomena. This degradation is a gradual process which interrupts electrical contact to the CE terminus leading to changes in migration times, instability of the CE current, and an unstable electrospray (Wahl and Smith 1994).

Another approach to sheathless CE-MS coupling is that of Fang et al. (1994) in which electrical contact to the CE capillary terminus is made by inserting a platinum wire into the outlet of the CE column. While an advantage of this technique is its ruggedness, however, there are two disadvantages associated with this method: the potential of arcing between the wire at the CE outlet and the inlet of the mass spectrometer and a non-uniform spray at the CE capillary terminus.

2.0 SUMMARY OF THE INVENTION

The present invention concerns a new sheathless CE/ESI interface which utilizes the advantages of previous techniques while eliminating many of the disadvantages, particularly in providing a rugged and durable interface that is currently not available. Presently used interfaces do not allow for routine analyses and are limited in use to highly sophisticated research laboratories. The interface of the present invention retains sensitivity and functional advantages of the CE/ESI-MS system while providing the advantage of withstanding the repositioning and manipulation of the interface required in optimizing measurements.

A new feature of this interface is the placement of the electrode wire inside of the CE capillary through a hole in the CE capillary wall. Previous designs of the CE/ESI-MS interface can be divided into two categories, sheathed and sheathless. In the sheathed designs, the electric contact to the CE capillary terminus is established by contact between the sheath liquid and the liquid content of the CE capillary at the terminus. This type of interface is represented by a coaxial sheath flow interface developed by Smith and co-workers (1988; 1991). Several sheathless interface designs have been utilized each with its own unique properties: (1) the low voltage end of the CE capillary was terminated within a stainless steel capillary as reported by Olivares and co-workers; (2) a gold conductive coating at the CE capillary terminus to establish electrical contact with the CE effluents developed by Wahl, et al.; (3) Zare and co-workers' design established electrical contact with the effluents at the ESI end of the CE capillary by inserting a platinum wire into the opening of the capillary terminus; (4) more recently, Joanne and co-workers developed an interface in which the terminus of the CE capillary and a short ESI emitter capillary are connected and sheathed by polysulphone microdialysis tubing. The disclosed sheathless interface differs from other technology in appearance and function.

The design of the disclosed interface has several advantages over previous designs. First, the design is more durable than other designs. The platinum wire is securely fastened within the capillary and can, therefore, withstand much more repositioning and movement than previous designs could without breaking. Next, the design affords a stable CE current since electrical contact is established by way of a wire rather than by way of a sheath liquid. This advantage allows for the best possible CE separation. Additionally, the design has no dead volume within the interface. This ensures the best resolution from the CE separation whereas most designs have dead volume which leads to peak broadening. Finally, the design does not interfere with the electrospray process since the platinum wire does not enter through the CE capillary terminus as it does in other designs.

3.0 BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1 A schematic of the in-capillary electrode interface for CE/ESI-MS, showing the end (outlet) of the CE column.

FIG. 2 Total ion electropherogram of a protein mixture using the in-capillary electrode CE/ESI-MS sheathless interface. A, gramicidin S; B, myoglobin; and C, cytochrome c. Unmarked peaks were not identified.

FIG. 3 CE/ESI-MS spectra corresponding to the peaks of FIG. 2. FIG. A, gramicidin S; FIG. B, myoglobin; and FIG. C, cytochrome c.

FIG. 4 Comparison between the UV electropherograms of a peptide mixture (standard C) using a 75 μm i.d., 80 cm long capillary (50 cm to UV): one (A) without in-capillary electrode, and the other one (b) with in-capillary electrode. 1, GY; 2, methionine enkephalin; 3, leucine enkephalin; 4, VYV; and 5, angiotensin II.

FIG. 5 The effect of methanol on the integrity of the epoxy. (A) 0.01 M acetic acid. (B) 0.01 M acetic acid with 10% methanol.

FIG. 6 The effect of the pH of the acetic acid buffer on CE/ESI-MS performance. (A), pH 2.0; (B), pH 3.4; (C), pH 5.0. 1, AESE; 2, FV; 3, morphiceptin; 4, VHLTPVEK; 5, bradykinin, and 6, cytochrome c.

FIG. 7 A comparison between CE/ESI-MS performance obtained using 50 μm i.d. (A) 30 μm i.d., and (B) APS-treated CE capillaries.

FIG. 8 Total ion electropherogram of protein standard D using the in-capillary electrode CE/ESI-MS sheathless interface. 1, β-lactoglobulin A; 2, ribonuclease A; 3, myoglobin; 4, lysozyme; 5, cytochrome c.

FIG. 9 CE/ESI-MS spectra corresponding to the peaks of FIG. 8. (A), β-lactoglobulin A; (B), ribonuclease A; (C), myoglobin; (D), lysozyme; (E), cytochrome c.

FIG. 10 The total ion electropherograms obtained from tryptic digests of horse heart cytochrome c (A) and myoglobin (B). See TABLEs 1 and 2 for the m/z and sequence of each peak. *, unidentified peaks.

FIG. 11 CE/ESI-MS analysis of red blood samples. Injections of approximately (A), 10 pmol; (B), 1 pmol; (C), 100 fmole; (D), 10 fmole.

FIG. 12 Mass spectra of α and β, hemoglobin corresponding to the peaks of FIG. 12C. (A), α hemoglobin, (B), β hemoglobin, and *, unidentified peaks.

FIG. 13 Reconstructed ion electropherograms (RIE) of the tryptic digest fragments of horse heart cytochrome c (A) and myoglobin (B) using CE/ESI-TOF-MS. Peaks marked with * and ** represent the reference compounds, Ultramark 1621 and MRFA, respectively.

FIG. 14 Tandem mass spectrum of a 14-residue peptide, TGQAPGFTYTDANK, using an in-source CID showing an intense Y" fragment ion series. Peaks marked with * were due to the co-eluting peptide m/z 964.529 and its CID fragments.

FIG. 15 CE/ESI-MS of the selected ion electropherograms of a peptide mixture under different programmed pressures using the single ion monitoring mode. Experimental conditions: A, −30 kV and 0.5 psi pressure; B, −30 kV, pressure maintained at 0.5 psi for the first 22 minutes then ramped to a final pressure of 3.8 psi at a rate of 0.6 psi/min; C, −30 kV, the pressure increased from 0 to 2.0 psi at a rate of 0.33 psi/min for the first 6 minutes, maintained at 2.0 psi for 9 minutes, then ramped to 4.0 psi at a rate of 0.72 psi/min. Other conditions:

- −10 kV electrokinetic injection with a duration of 5 seconds; a 1 10 cm long, 75 -μm-i.d., 150 μm o.d. CE capillary; an acetic acid buffer (0.01 M, pH 3.2); CE inlet voltage −30 kV, electrospray voltage +3.5 kV. A, Leu-gly; B, Val-asp; C, Phe-val;
- D, Leu-phe; E, Gramicidin S.

FIG. 16 Total ion electropherograms (TIE) of the tryptic digest fragments of hemoglobin S using CE/ESI-TOF-MS. Peaks marked with * and ** represent the reference compounds, AGSE and MRFA, respectively. See TABLE 6 for the m/z and the sequence of each peak.

FIG. 17 Calibrated mass spectra of the peak 16 in FIG. 16 which corresponds to the VHLTPVEK, the eight N-terminal residue peptide of HbS.

FIG. 18 Tandem mass spectrum of a 8-residue peptide (VHLTPVEK, the eight N-terminal residue peptide of HbS), using an in-source CID showing an intense Y" fragment ion series.

3.1 BRIEF DESCRIPTION OF THE TABLES

TABLE 1

Tryptic Digests of Horse Cytochrome c in the m/z Range of 500–1000. Acetyl-DVEKGKKIFVQKCAQCHTVEK (heme)GGKHKTGPNLHGLFG RKTGQAPGFTYT-DANKNKGITWKEETLMEYLENPKKY-IPGTKMIFAGIKKK TEREDLIAYLKKATNE (SEQ ID NO: 1) (104 amino acids, MW=12359.8 Da).

TABLE 2

Tryptic Digests of Horse Heart Myoglobin in the m/z Range of 500–1000. GLSDGEWQQVLNVWGKVEADI-AGHGQEVLIRLFTGHPETLEKFDKFKHLKT EAEMKASEDLKKHGTVVLTALG-GILKKKGHHEAELKPLAQSHATKHKIPIK YLEFIS-DAIIHVLHSKHPGDFGADAQGAMT-KALELFRNDIAAKYKELGFQG (SEQ ID NO: 2) (153 amino acids, MW=16951.5 Da).

TABLE 3

Measured masses of tryptic digests of horse cytochrome c in the m/z range of 500–1000. Acetyl-GDVEKGKKIFVQKCAQCHTVEK (heme) GGKHKTGP-NLHGLF GRKTGQAPGFTYTDANKNGITW-KEETLMEYLENPKKYIPGTKMIFAGIKK KTEREDLIAYLKKATNE (SEQ ID NO: 3) (104 amino acids, calculated average MW 12359.80 Da).

TABLE 4

Measured masses of tryptic digests of horse heart myoglobin in the m/z range of 500–1000. GLSDGEWQQVL-NVWGKVEADIAGHGQEVLIRLFTGH-PETLEKFDKFKHLKT EAEMKASEDLKKHGTVVLTALG-
GILKKKGHHEAELKPLAQSHATKHKIPIK YLEFIS-
DAIIHVLIHSKHPGDFGADAQGAMT-
KALELFRNDIAAKYKELGFQG (SEQ ID NO: 4) (153 amino acids, calculated average MW 16951.53 Da).

TABLE 5

Measured masses of the collisionally induced fragments of tryptic digests of cytochrome c in the m/z range of 350–1500 using in-source fragmentation.

TABLE 6

Measured masses of tryptic digests of hemoglobin S in the m/z range of 350–1500.

4.0 DESCRIPTION OF ILLUSTRATIVE EMBODIMENTS

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. Moreover, all of the methods and apparatus disclosed and claimed herein can be made and executed without undue experimentation. However, those of skill in the art should, in light of the present disclosure, appreciate that many changes can be made in the specific embodiments which are disclosed and still obtain a like or similar result without departing from the spirit and scope of the invention.

5.0 EXAMPLES

5.1 Example 1

Materials and Methods

In a first reduction to practice of the present invention, CE capillary columns were prepared from 75 $\mu$m-i.d., 150 $\mu$m-o.d. capillary columns (Polymicro Technology, Phoenix, Ariz.). A microscope (0.7 to 4.2×) (AO Instrument Company, Buffalo, N.Y.) was used for construction of the capillary. The fabrication procedure was as follows.

A 50 $\mu$m-diameter platinum (Pt) wire (Goodfellow, Berwyn, Pa.) was inserted approximately 4 cm inside one end of the CE column, hereafter called the CE outlet (as opposed to the inlet). Using a 2.22 cm-diameter abrasive disk (Small Parts Inc., Miami Lakes, Fla.) attached to a drill (DREMEL, Racine, Wis.), a small opening was made into the wall of the column approximately 2 cm from the CE outlet. Preliminary data indicated no noticeable difference in results when the hole was made in the range of 1.5–2.5 cm from the CE outlet. The 50 $\mu$m-diameter Pt wire prevented the capillary from breaking during the cutting process.

After the opening was made, the 50 $\mu$m-diameter Pt wire was retracted (approximately 2.5 cm) until it was slightly beyond the new opening. A 25 $\mu$m-diameter Pt wire was inserted 0.2–0.3 cm into the column through the cut. The 50 $\mu$m-diameter Pt wire was then slowly pushed back into the capillary, passing the opening by about 0.3 cm, bending the 25 $\mu$m-diameter wire toward the inner wall (FIG. 1). The cut was then sealed using epoxy (APS replacement adhesive, Mecum Group, Waltham, Mass.), thereby securing the 25 $\mu$m-diameter wire in place. The 50 $\mu$m-diameter wire prevented the epoxy from penetrating into the CE column and clogging the column. After about five minutes, while the epoxy was still flexible, the 50 $\mu$m-diameter wire was very carefully drawn completely out of the column. To ensure the CE capillary remained unclogged, nitrogen gas was passed through it until the epoxy was cured.

Using a flame, 0.5 cm of the outside polyimide coating at the terminus of the capillary was removed. To sharpen the tip of the CE column, the exposed fused silica portion of the tip was etched with a 50% hydrofluoric acid (HF) solution for about 15 minutes. Helium gas was passed though the column during the etching process to minimize enlargement of the CE outlet.

A similar CE capillary was also prepared with a gold coated tip using a sputter deposition system (Materials Research Corporation, Orangeburg, N.Y.).

It has been determined in subsequent experiments that 1 $\mu$m to 10 $\mu$m Pt wires may also be used for the electrode inside the CE capillary column. Moreover, CE capillary columns having smaller i.d.s, such as 50 $\mu$m and 30 $\mu$m may also be used. In fact, smaller i.d. capillary columns offer certain advantages over the larger i.d. capillary columns as will be discussed in detail subsequently. Generally, narrower capillaries enhance the sensitivity of detection in sheathless CE-MS interfaces. It should be noted that as smaller i.d. capillaries are used in practicing the invention, the diameter of the electrode should also be reduced so that the presence of the electrode inside the capillary column does not clog the column. The diameter of the electrode should be at least smaller in diameter than the i.d. of the capillary column, and preferably as small as practicable.

For the CE separations of small peptides, a 45 cm-long capillary was used in which the inner wall was chemically modified with aminopropylsilane (APS) according to the procedure of Figeys et al. (1996). This procedure, however, did not produce adequate separation for large peptides and for proteins. For these analyses, a longer column (80 cm) was used in which the inner wall of the CE capillary was derivatized using the APS derivatization procedure developed by Moseley et al. (1992). For the studies presented here, the chemical modifications were performed prior to the insertion of the Pt wire. The APS derivatization following Pt wire insertion has also been performed, but within combined experimental errors, the difference in results were insignificant.

As a result of the APS surface modification and the acidic buffer solution used, the inner wall of the capillary has a net positive charge. This results in an electroosmotic flow in the opposite direction of uncoated fused-silica capillaries. Therefore, for small peptides, electrophoresis was performed at an applied potential of −278 V/cm (−9.0 kV at the CE capillary inlet and +3.5 kV at the electrospray terminus). For protein analysis, the applied potential for the CE separation was −288 V/cm (−20.0 kV at the CE capillary inlet and +3.0 kV at the CE electrospray terminus). The buffer solution (0.01 M acetic acid) was prepared using distilled water (Barnsted NANOpure II, Boston, Mass.) and acetic acid (Baxter Healthcare Corporation, McGaw Park, Ill.).

Sodium hydroxide (NaOH), hydrochloric acid (HCl), and hydrofluoric acid (HF) solutions were purchased from Fisher Scientific Company (Fair Lawn, N.J.). Argon and helium gases were purchased from Wilson Oxygen & Supply Co., Inc. (Austin, Tex.). All other chemicals (including peptides, proteins, and APS) were purchased from Sigma Chemical Company (St. Louis, Mo.) and used without further purification. All solutions were filtered through a syringe filter 13 mm/0.5 $\mu$m (Baxter Scientific, Grand Prairie, Tex.). The CE instrument used was a P/ACE System 2100 (Beckman Instruments, Fullerton, Calif., USA) operating with Beckman System Gold software. The running buffer for all CE separations was a 0.01 M acetic acid aqueous solution (pH=3.2). Prior to each set of measurements, the capillary was conditioned with the buffer for 5 minutes. For all sample injections, the outlet of the CE capillary was held at ground potential. The ESI interface used for these studies was built in house (Jackett and Moini 1994) for a Finnigan MAT TSQ 70 mass spectrometer (San Jose, Calif.).

5.2 Example 2
Stability of Contact at CE Terminus

The stability and reliability of the electrical contact at the CE terminus is an important aspect for successful electrophoresis. With the inventors' design, electrical contact is reliably maintained by placing the electrode inside the CE capillary through a small hole in the capillary wall near the terminus. This electrode acts both as the low voltage electrode of the CE electric circuit and as a connection for the electrospray ionization voltage.

The stability of the CE current was tested for the in-capillary electrode CE/ESI-MS sheathless interface utilizing the column and parameters established above for small peptide analysis. The CE current was stable at 2.5 $\mu$A ±0.25 $\mu$A for 50 minutes (maximum time studied).

Unlike other sheathless interfaces in which the CE capillary tip either is gold coated or has a wire that is inserted into the outlet of the CE capillary, with the inventors' in-capillary electrode design, stable CE and electrospray currents were achieved over long periods by simply sharpening the fused silica tip of the CE capillary. With no metal at the tip, one can place the capillary terminus much closer to the inlet of the mass spectrometer with minimal arcing possibility.

The electrospray ion signal intensity of a column with a bare fused silica tip was compared to that of a column with a gold-coated tip using the in-capillary electrode design for both columns. It was found that, within the experimental error, the intensities and stability of the ESI ion signals were similar for both tips. Additionally, no noticeable background chemical noise due to direct contact between the epoxy and the electrolyte solution was observed in the mass range studied. Moreover, since some CE separations require a CE buffer containing 10% methanol (Figeys et al. 1996), several CE/ESI-MS experiments were performed under this condition, and no sign of epoxy deterioration was observed.

5.3 Example 3
Performance Evaluation

To evaluate the overall performance of the sheathless in-capillary electrode electrospray interface design, a mixture containing three dipeptides (Val Asp, PheVal, LeuPhe) and one eight residue peptide, ValHisLeuThrProValGluLys (0.1 mg/mL each peptide) was electrokinetically injected into the capillary using −5.0 kV potential difference across the capillary with a duration of 5 seconds. All compounds were resolved and detected in less than four minutes. The mass spectra of each peak of the electropherogram showed a protonated molecule as the base peak for the dipeptides and the doubly charged ion as the base peak for the eight residue peptide.

For this experiment, the mass spectrometer was operated under a wide scan mode (180–480 mass-to-charge (m/z), 1 sec/scan).

The utility of this design for protein and peptide analysis was demonstrated by analysis of a mixture containing 0.25 mg/mL myoglobin (MW=16,951 Dalton (Da)), cytochrome c (MW=12,360 Da), and gramicidin S (MW=1,141 Da) in $H_2O+CH_3OH+CH_3COOH$ (47:47:6, v/v). The injection was performed using −5.0 kV potential difference across the capillary with a duration of 3 seconds. Under these injection conditions, approximately 140 fmole of each, myoglobin and cytochrome c, and 2.6 pmol of gramicidin S were injected into CE capillary (Joregenson and Lukacs 1983). The mass spectrometer was operated under a wide scan range (550–1300 m/z, 2.0 sec/scan).

FIG. 2 shows the total ion electropherogram obtained from the analysis of this mixture, and FIG. 3A, FIG. 3B and FIG. 3C show the corresponding mass spectra. Comparison of the results presented in FIG. 2 and FIG. 3 with those previously reported for a similar mixture using sheathed CE/ESI-MS (Moseley et al. 1992) indicates that the in-capillary electrode design exhibits higher sensitivity and lower background chemical noise. In addition, because of the in-capillary electrode design, there is no dead volume at the interface.

Under the experimental conditions explained above, a detection limit of approximately 4 femtomoles (signal-to-noise ratio (S/N)=3) was achieved for myoglobin. This detection limit is lower than some CE-MS studies where a 75 $\mu$m-i.d. column and wide scan range mode were used (Moseley et al. 1992, Banks, 1995). However, these results are comparable to or, in some cases, less sensitive than results of some other CE/ESI-MS experiments where a narrower capillary and/or selected ion monitoring (SIM) mode were used (Severs, et al. 1996, Figeys et al. 1996, Valaskovic et al. 1996). Considering the fact that the presently reported detection limit was achieved utilizing a 75 $\mu$m-i.d. CE column and using a wide scan range of m/z 550–1300, a considerably lower detection limit is expected when a narrower capillary and/or SIM mode are employed.

5.4 Example 4
Effects of Various Parameters on the CE/ESI-MS Interface

The parameters investigated include the length of the Pt wire inside the CE capillary and its position with respect to the CE outlet, the effect of the epoxy used to seal the capillary hole and to secure the in-capillary electrode, the effect of the inner diameter of the CE capillary on sensitivity of detection, and the effect of buffer solution pH on the performance of the CE/ESI-MS. The sheathless interface according to the present invention was further evaluated through the analysis of complex mixtures ranging from small peptides and proteins to tryptic digests of proteins. In addition, the utility of this interface for the analysis of real-world samples was demonstrated by analyzing whole human blood.

5.4.1 Equipment

The CE instrument used was a P/ACE System 2100 (Beckman Instruments, Fullerton, Calif.) operating with Beckman System Gold software. Except when otherwise mentioned, the running buffer for the CE separations was an aqueous 0.01 M acetic acid solution (pH=3.4). Prior to each set of measurements, the capillary was conditioned with this buffer for 5 minutes.

The preparation of the in-capillary electrode CE/ESI-MS interface as described above was followed, although thinner diameter wire was used for the electrode. Briefly, a 10 $\mu$m diameter Pt wire was inserted into a small hole near the outlet of the CE capillary. The hole was then sealed using epoxy, which also secured the in-capillary electrode. In this set of experiments, 75, 50, and 30 $\mu$m i.d. APS-treated capillaries were employed. A 50 $\mu$m i.d. APS-treated CE capillary was used for all experiments unless otherwise mentioned.

The vacuum interface to couple ESI with MS is a modified version of a previously designed vacuum interface for a Finnigan MAT TSQ 700 mass spectrometer (San Jose, Calif.). The modifications include a shorter (12 cm) heated capillary and the addition of a second stage of mechanical pumping similar to the design recently reported by this laboratory [Jiang and Moini 1995]. The mass spectrometer was operated in either wide scan mode or in multiple-ion monitoring mode. In multiple-ion monitoring mode, 3 m/z values were selected using a mass window of 5 Da and an integration time of 0.30 second (s) for each mass window.

5.4.2 Materials

The buffer solution (0.01 M acetic acid, pH 3.4) was prepared using distilled water (Barnsted NANOpure II, Boston, Mass.) and glacial acetic acid (Baxter Healthcare Corporation, McGaw Park, Ill.). The hydrochloric acid (HCl) and hydrofluoric acid (HF) solutions were purchased from Fisher Scientific Company (Fair Lawn, N.J.). Nitrogen gas was purchased from Wilson Oxygen & Supply Co., Inc. (Austin, Tex.). Modified trypsin (Promega, Madison, Wis.) was used for protein digestion [Takada et al. 1994]. All other chemicals including peptides, proteins, and APS were purchased from Sigma Chemical Company (St. Louis, Mo.) and used without further purification.

Three peptide standard solutions were used in these studies. Two standard solutions (A and B) were prepared by: A) dissolving 2.0 mg of each peptide (AESE, 362.3 DA; FV, 264.3 Da; morphiceptin, 521.6 Da; VHLTPVEK, 922.1 Da; bradykinin, 1060.2 Da; and cytochrome c, 12359.8 Da) in 10 mL of a methanol+water+acetic acid solution (47:47:6, v/v); and B) 2.5 mg of each peptide (AESE, FV, morphiceptin, and bradykinin) in 10 mL of the same sample. The third standard (C) was Sigma's HPLC peptide standard, which is composed of approximately 0.125 mg GY (238.2 Da), 0.5 mg each of VYV (379.5 Da), methionine enkephalin (573.7 Da), leucine enkephalin (555.6 Da), and angiotensin II (1046.2 Da). Sigma's HPLC peptide standard was dissolved in 1 mL. of pure water. The protein standard (standard D) contained 0.2 mg each of β-lactoglobulin A, ribonuclease A, myoglobin, lysozyme, and cytochrome c in 1 mL of 0.01 M acetic acid solution. All solutions were filtered through a 13 mm/0.5 $\mu$m syringe filter (Baxter Scientific, Grand Prairie, Tex.).

The tryptic digests utilized an enzyme-to-substrate ratio of approximately 1:30 in a 0.05 M ammonium bicarbonate (pH 8.1) solution kept at 37° C. for 16 hours. The digest was then dried in a vacuum centrifuge and redissolved in a water+methanol solution (50:50, v/v) containing 3 mM formic acid with an approximate sample concentration of 50 $\mu$M.

Fresh human blood was obtained from a healthy adult male. Samples of this blood were prepared by diluting 4 $\mu$L aliquots with 0.01% aqueous acetic acid (pH 3.4) to the following ratios: 1:15, 1:150; 1:1500, and 1:15000. No purification step was used. These samples were injected into the CE column using 1.0 psi pressure for a duration of 3 seconds. Assuming a 15 g/100 mL concentration of hemoglobin in normal blood, the amounts of hemoglobin injected into CE column were approximately 10 pmol, 1 pmol, 100 fmol, and 10 fmol, respectively, for the diluted blood. The blood experiments were performed on a newly acquired ESI/TOFMS, Mariner (PerSeptive Biosystems, Framingham Mass.). For this study, the mass spectrometer operated in the m/z range of 500–2000 at a rate of 8000 acquisitions/second, which led to the generation of a single spectrum every second.

5.4.3 Effects of the In-capillary Electrode on the Performance of the CE Separation An important feature of the in-capillary electrode design is that there is no dead volume at the interface. As a result of the Pt wire inside the capillary, the inner diameter of the CE capillary where the Pt wire is inserted actually decreases. It should be noted that the i.d. of the capillary is only reduced where the electrode is present, but that this reduction in no way reduces the capillary i.d. at its outlet end. In this set of experiments, 10 $\mu$m diameter Pt wires are used to construct the in-capillary electrodes. Use of this size wire reduces the i.d. of the capillary by approximately 10 $\mu$m and the cross-sectional area of the capillary by approximately 10%. The actual reduction depends not only on the outer diameter of the Pt wire used, but also on how much the glue penetrates inside the capillary. Total reduction is examined by an experiment, such as one reported below. This change in the effective i.d. of the CE capillary could be reduced by using a narrower wire. For example, current experimental work is using 1 $\mu$m wire for narrower capillaries, but the following experimental results are based on 10 $\mu$m wire.

To investigate the effects of this partial reduction of the capillary i.d. on the CE separation performance, two experiments were conducted using the UV detector of the CE instrument at a wavelength of 214 nm. Two 75 $\mu$m i.d., 80 cm long (50 cm long from inlet to UV detector) APS-treated capillaries were employed, one containing an in-capillary electrode and one without. A 1:10 dilution of peptide standard C was used for this experiment. In both capillaries, sample was injected using a pressure injection mode (0.5 psi) with a duration of 1.2 seconds. Due to the diameter reduction of the capillary at the position where Pt wire was inserted, the amount of sample injected into the capillary was approximately 80% of that injected into the capillary without Pt wire (FIGS. 4A and 4B).

For this experiment, the end of the CE capillary without the in-capillary electrode was placed in the buffer solution and the end of the capillary with the in-capillary electrode was grounded at the wire. A field strength of −375 V/cm was employed for CE separation. Comparison between the two resulting UV electropherograms (FIG. 4) indicated that a better separation efficiency and a slightly longer separation time were obtained with the in-capillary electrode capillary (FIG. 4B) compared to the capillary without the in-capillary electrode (FIG. 4A), which are attributed to lower electroosmotic flow (EOF) in the former capillary.

5.4.4 Effect of Length and Position of the Electrode

This set of experiments showed that changing the length of the Pt wire inside the CE capillary from approximately 0.1 to 3.5 cm had no noticeable effects on the CE/ESI-MS performance. Additionally, while preliminary data indicated no noticeable difference in results when the hole was made in the range of 1.2 to 2.5 cm from the CE outlet, the latter experiments showed that varying the position of the hole where the Pt electrode is inserted into the capillary from 1 to 4 cm also had no significant effect on CE separation. It is expected that the position of this hole may be up to 10 cm from the outlet end without significantly affecting CE separation.

It should be noted that an electrode may also be inserted near the inlet end of the CE capillary. The presence of an in-capillary electrode near the inlet end helps to attract/inject ions into the capillary. This will also help to miniaturize the injection port of the CE and also eliminate the need for an external electrode in the sample vial.

5.4.5 Effect of Epoxy

Since epoxy was used to secure the Pt wire and seal the hole where the Pt wire was inserted into the capillary, the contribution of epoxy to the background chemical noise in the m/z range of 250–2000 was investigated. The direct contact between the epoxy and the aqueous 0.01 M acetic acid solution did not produce any noticeable background chemical noise within the mass range investigated. Because some researchers add methanol to their buffer to decrease the EOF, the effect of methanol on the integrity of the epoxy and background chemical noise was also studied.

The CE separations of standard B was compared using (1) a 0.01 M acetic acid buffer solution containing 10% methanol; and (2) a pure 0.01 M acetic acid buffer solution. Approximately the same amount of sample was injected into the capillary for each analysis using a pressure injection mode (1.5 psi) with a duration of 3 seconds. Under these conditions, approximately 3.9 picomoles AESE, 5.3 picomoles FV, 2.7 picomoles morphiceptin, and 1.3 picomoles bradykinin were injected into the CE capillary. The CE was operated under −375 V/cm field strength.

As expected, the migration times of the peptides in the methanol-containing buffer solution increased (FIG. 5). In addition, a slightly better S/N was observed when methanol was present. However, no sign of epoxy deterioration was observed due to the presence of methanol.

5.4.6 Effects of pH

The effects of the buffer solution pH on the CE/ESI-MS analysis of standard A is shown in FIG. 6. Three acetic acid solutions at pH's 2.0, 3.4, and 5.0 were used. Approximately the same amount of sample was injected into the capillaries for each analysis using a pressure injection mode (1.5 psi) with a duration of 3 seconds (approximately 3.9 picomoles of AESE, 5.3 picomoles of FV, 2.7 picomoles of morphiceptin, 1.5 picomoles of VHLTPVEK, 1.3 picomoles of bradykinin, and 110 femtomoles of cytochrome c). The CE was operated under −375 V/cm field strength. The highest pH (pH 5.0), lowest ionic strength acetic acid buffer solution gave the shortest retention time with the poorest resolution, while the lowest pH (pH 2.0), highest ionic strength acetic acid buffer solution showed the highest resolution with the longest migration time.

5.4.7 Effect of Capillary Inner Diameter

The effects of narrower capillaries on the sensitivity of detection (S/N) was also studied using the in-capillary electrode design. It was found that the i.d. of the capillary had the most significant effect on the CE/ESI-MS analyses of peptide and protein mixtures. A 0.5 mg/mL solution of standard C (except 0.125 mg/mL GY) was used for this study. Standard C was injected into both CE capillaries using a pressure injection mode (1.5 psi, 3 seconds).

A significant enhancement in the sensitivity was observed as a result of the narrower capillary. The results are summarized in FIGS. 7A and 7B, where the S/N of the peptide mixture is compared using 50 μm i.d. and 30 μm i.d APS-treated capillaries. As shown in FIGS. 7A and 7B, even though the amount injected into the 30 μm i.d capillary (approximately 1.9 picomoles of VYV, 0.9 picomoles of methionine enkephalin, 0.9 picomoles of leucine enkephalin, and 0.5 picomoles of angiotensin II) was only 1/7.5 of that injected into the 50 μm i.d capillary, the S/N obtained using the 30 μm i.d. capillary was significantly higher than that obtained using the 50 μm i.d. capillary. With the quantity of sample injected here, the dipeptide (FV) was not detected with either capillary.

To examine the sensitivity of detection for proteins under different capillary i.d.s., the detection limits for myoglobin were compared using a 60 cm long, 50 μm i.d. APS-treated capillary and a 60 cm long, 30 μm i.d. APS-treated capillary. Under a wide scan m/z range of 500–1400, the detection limits for myoglobin using a 50 μm i.d. and 30 μm i.d. were approximately 1 femtomole and 600 attomoles, respectively. The results obtained for the 30 μm i.d. capillary were approximately an order of magnitude better than those reported previously using a 75 μm i.d. capillary. Compared to a wide scan mode, under multiple-ion monitoring mode, one order of magnitude lower detection limit (approximately 100 attomoles using the 50 μm i.d. column) was achieved for both cytochrome c and myoglobin.

5.4.8 Durability and Reproducibility

Overall performance of CE capillaries for CE/MS analysis depends on two major factors: 1) stability of the electrical connection at the CE outlet and 2) stability of the derivatization of the CE capillary inner wall. In-capillary electrode provides a robust and stable electrical connection to the CE outlet for many days. However, under continuous operation the APS coating of the derivatized capillaries has a short lifetime of only a few days (2–3 days). According to our experience, at this time the stability of the APS derivatization is the bottleneck and limiting factor in the performance of the CE for routine analysis of complex mixtures of peptides and proteins. The reproducibility of this CE/ESI-MS was investigated by analyzing a 0.1 mg/mL solution of gramicidin S. The relative standard deviation (RSD) of the height of the total ion current for five consecutive injections was 3.4%. For this experiment the mass spectrometer was scanned in the m/z range of 552–592 at a rate of 1 scan/sec. A 50 μm. 80 cm long APS-treated column, a −375 V/cm CE field strength, and a pressure injection (1.5 psi) mode with a duration of 3 seconds were used for these experiments.

5.4.9 Preferred Embodiment

As a result of the inventor's experimental work, one embodiment of a sheathless interface for capillary electrophoresis/electrospray ionization-mass spectrometry comprises a capillary column having a wall, an outlet end, and an opening in the wall. The opening is located near the outlet end of the capillary column. At least one electrode is disposed inside the capillary column through the opening in the wall of the capillary column. The electrode is affixed to that opening. The capillary column preferably has an inner diameter of 30 μm or less, and the electrode is preferably platinum wire having a diameter of 10 μm or less. The length of the electrode inside the capillary column is preferably 0.1 to 3.5 cm. The opening where the electrode is inserted into and attached to the capillary is preferably 1 to 10 cm from the outlet end. If there is more than one opening, then at least one of the openings is close to the outlet end. The outlet end of the capillary column is preferably a sharp tip. This sheathless interface may optionally have an in-capillary electrode inserted into the capillary near its inlet end.

5.5 Example 5

Application of the In-capillary Electrode to Analysis of Proteins

To evaluate the overall performance of the sheathless in-capillary electrode electrospray interface design, FIG. 8 shows the total ion electropherogram (TIE) of protein standard D using the in-capillary electrode CE/ESI-MS sheathless interface. A 50 μm i.d., 80 cm long APS-treated CE capillary was used. The CE separation electric field strength was −375 kV/cm. and the mass spectrometer was operated under an m/z range of 600–2000 at 1.5 scan/sec. Approximately 200 femtomoles of each protein were injected into the CE capillary using a pressure injection mode (1.5 psi for 3 seconds). The corresponding mass spectra for each peak in FIG. 8 is shown in FIG. 9. All proteins were resolved and detected in less than eight minutes.

Complex mixtures of peptides generated from the tryptic digestion of large proteins present a difficult analytical challenge because the fragments cover a wide range of both pI and hydrophobicity [Moseley et al. 1992]. To examine the performance of the in-capillary electrode design with regard to complex mixtures generated from tryptic digests of proteins, tryptic digests of horse heart cytochrome c and myoglobin were analyzed. For each separation, a 0.01 M acetic acid buffer (pH 3.4), and a 50 μm i.d., 80 cm long APS-treated CE capillary was used. The mass spectrometer was scanned in the m/z range of 500–1100 using a scan time of 1.5 scan/sec. Approximately 400 femtomoles of each tryptic fragments were injected into the capillary using a pressure injection mode (1.5 psi) with a duration of 3 seconds. FIGS. 10A and 10B show the total ion electropherograms of the tryptic digests of horse heart cytochrome c and myoglobin, respectively. TABLEs 1 and 2 list the main tryptic digest fragments of cytochrome c and myoglobin as well as their sequences.

5.6 Example 6
Analysis of Human Blood

Recently, matrix assisted laser desorption time-of-flight mass spectrometry (MALDI-TOFMS) was applied to the analysis of whole human blood [Houston et al. 1997; Li et al. 1996; Lapolla et al. 1997]. However, no separations were used for these studies. In order to demonstrate the utility of the in-capillary electrode sheathless interface in the analysis of real-world samples, whole human blood was analyzed using CE/ESI-MS. A 30 μm i.d., 50 cm long APS-treated capillary was used for this study and the CE was operated under −640 V/cm field strength. The diluted blood samples were injected into the CE column using pressure injection mode.

Figure 1:
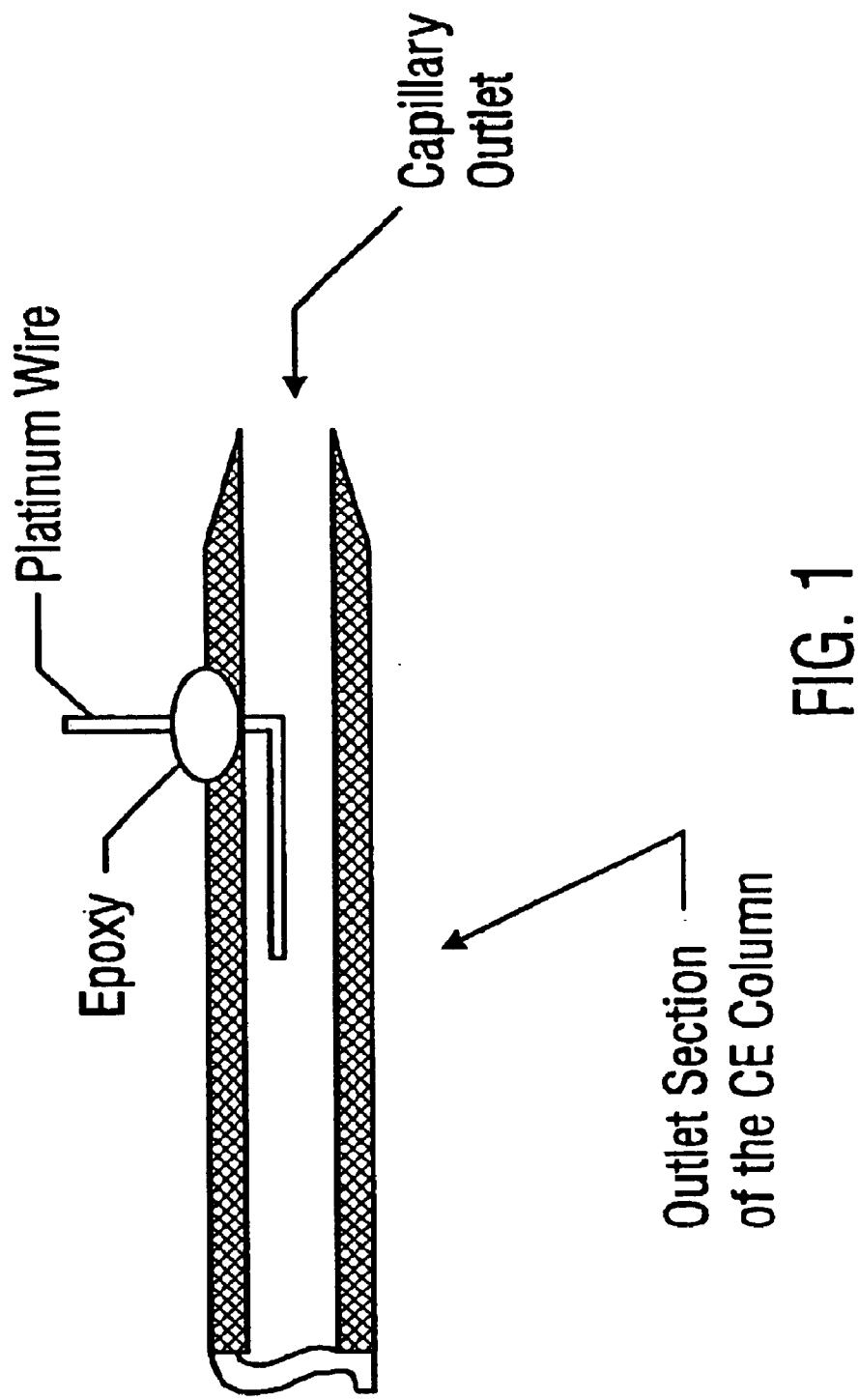
Figure 2:
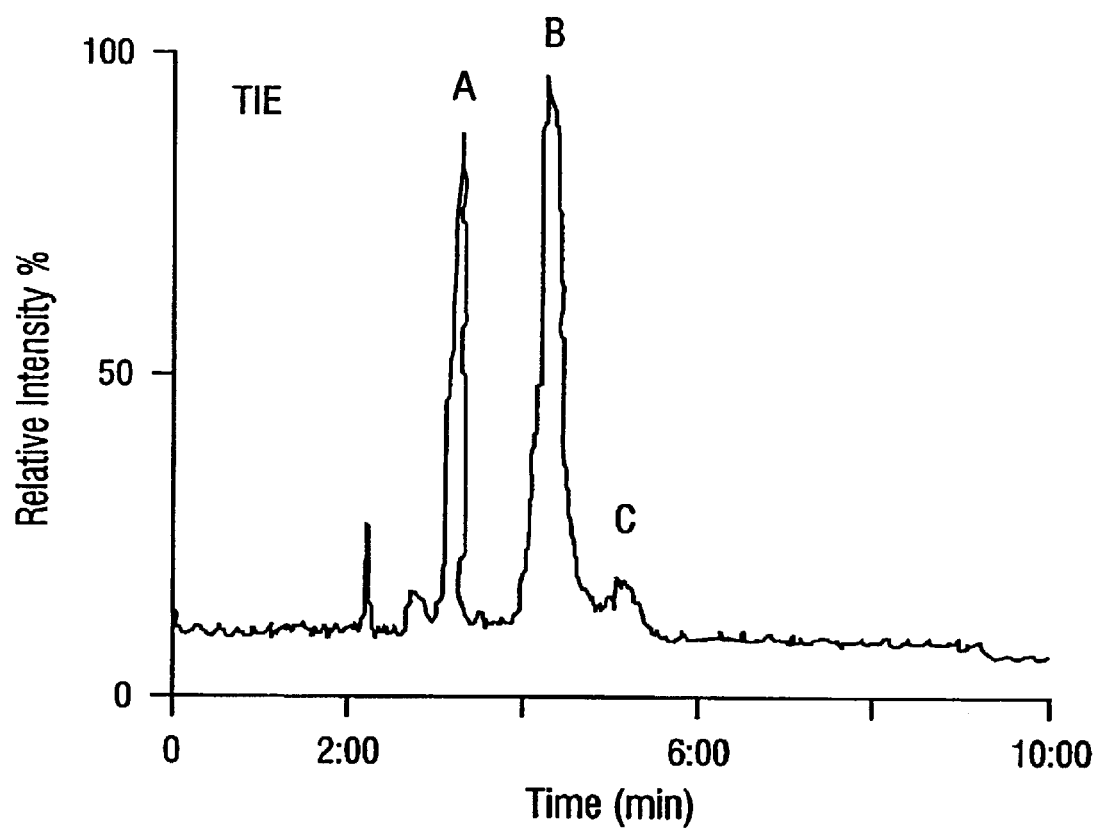
Figure 3A:
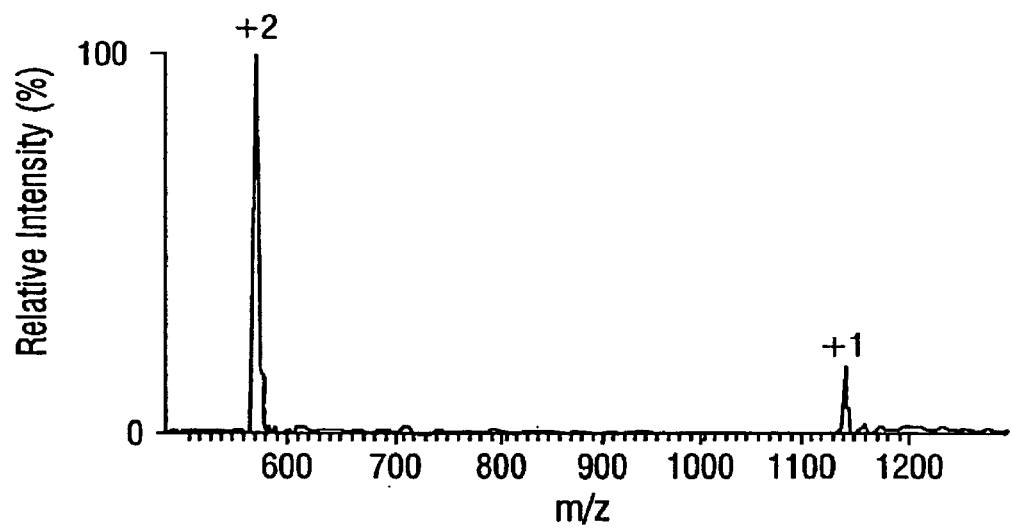
Figure 3B:
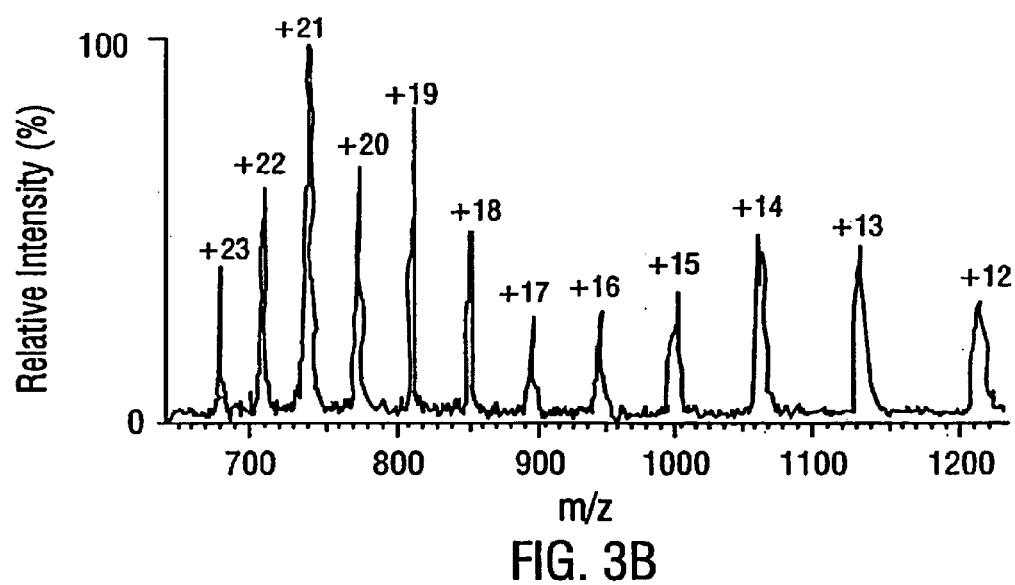
Figure 3C:
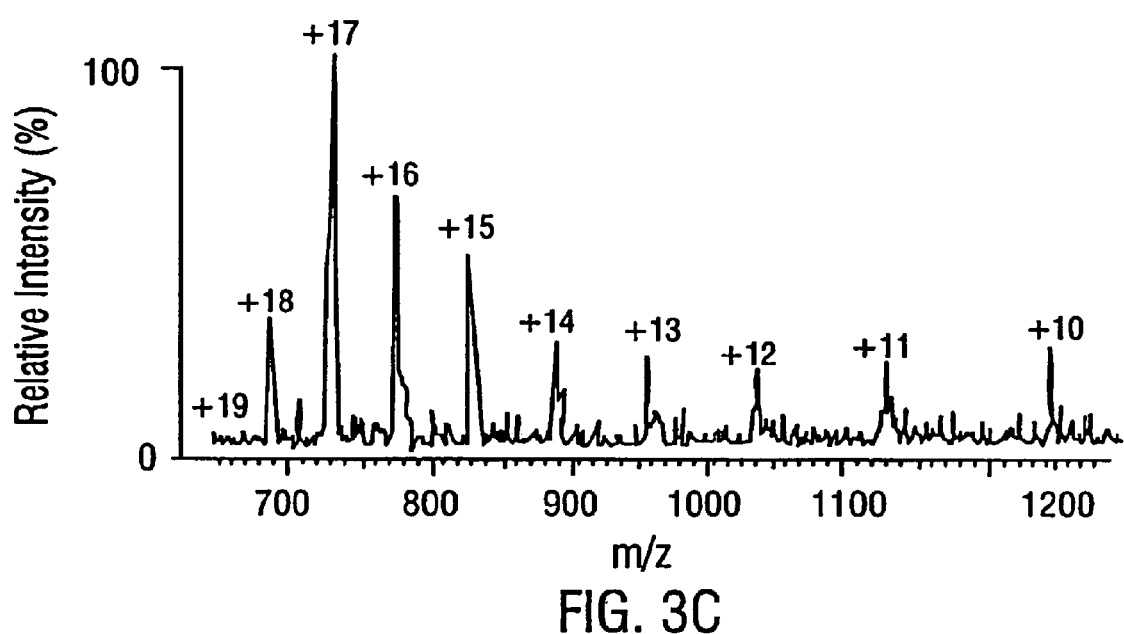
Figure 4A:
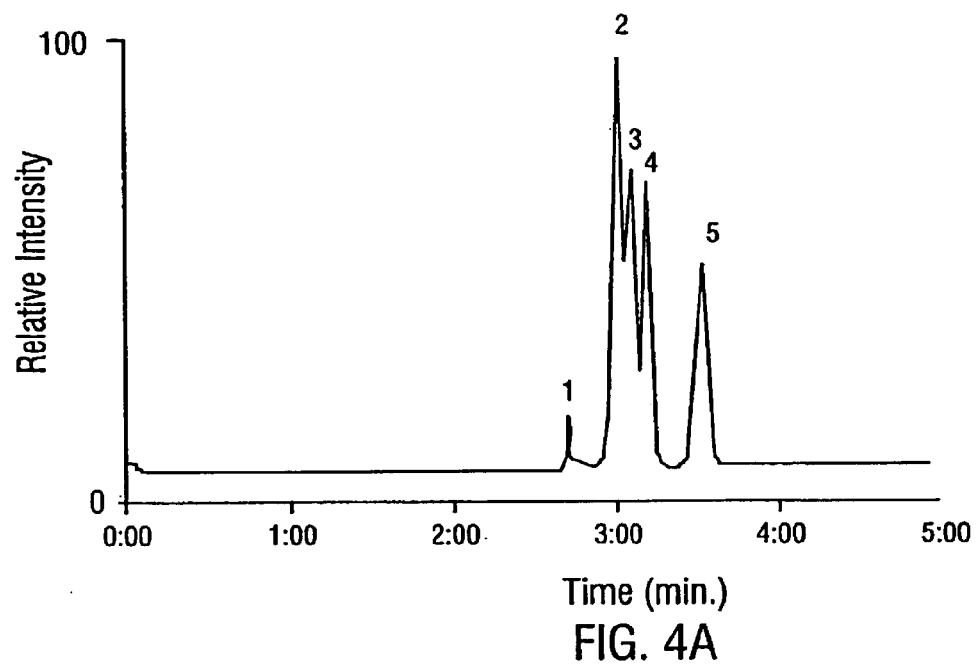
Figure 4B:
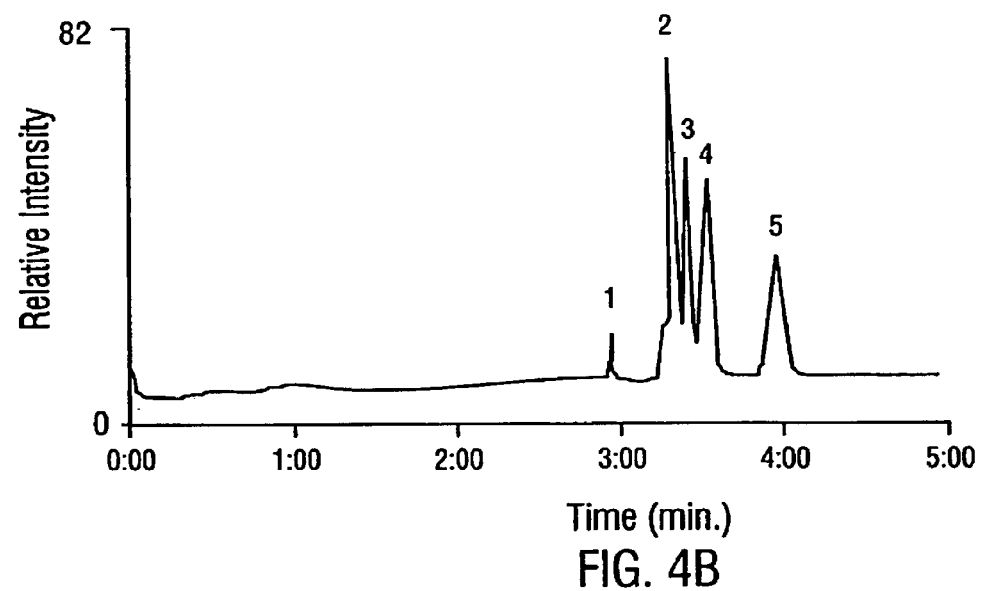
Figure 5A:
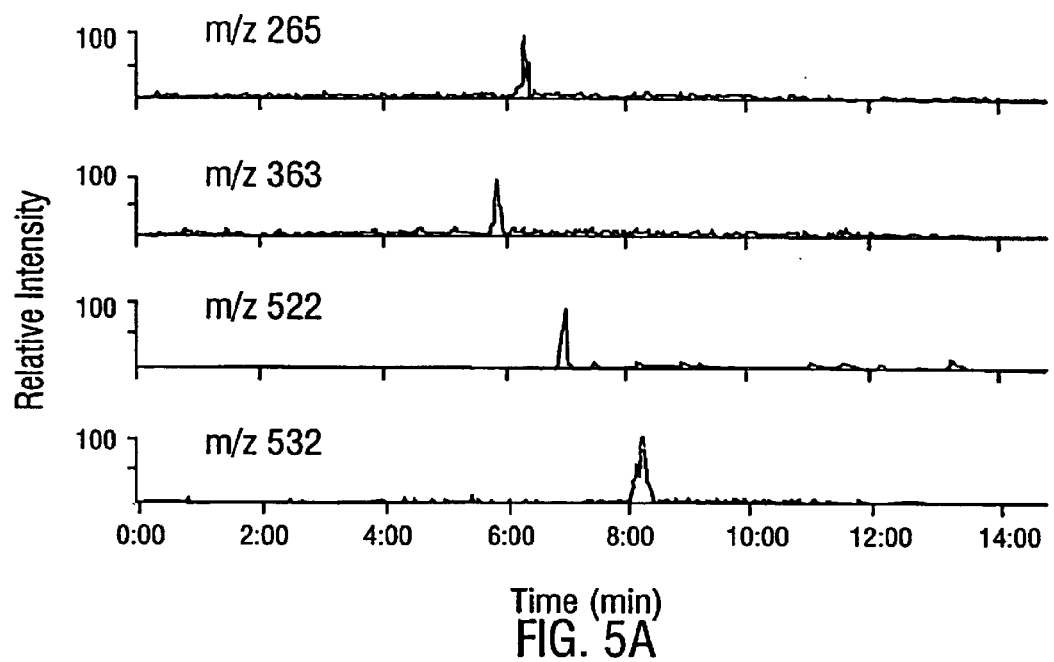
Figure 5B:
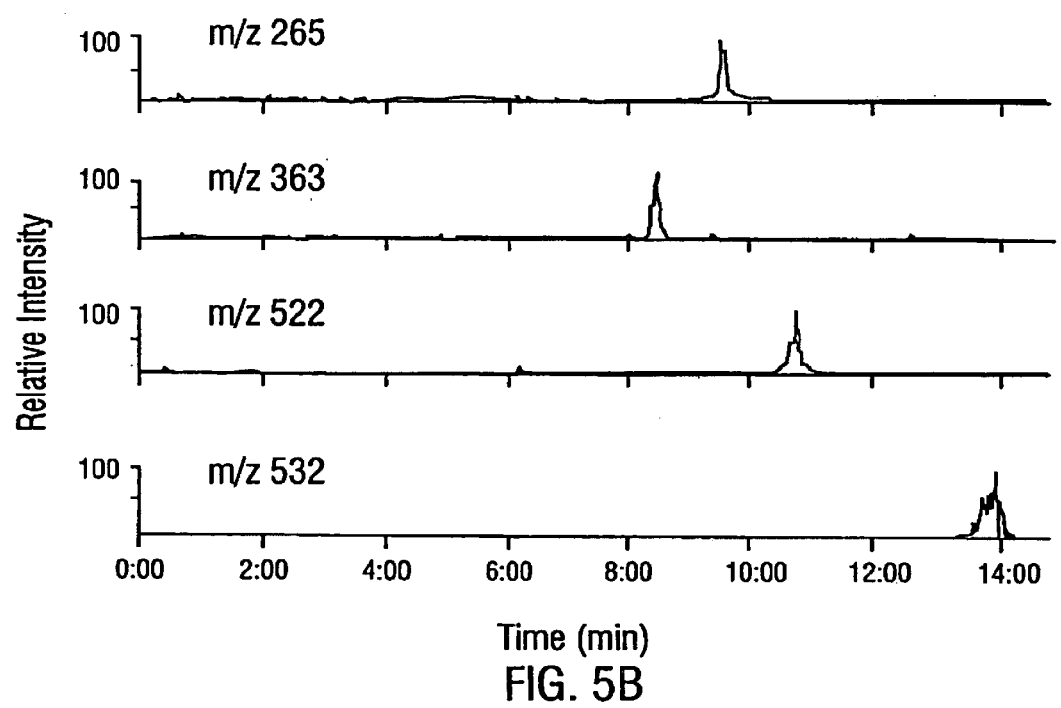
Figure 6A:
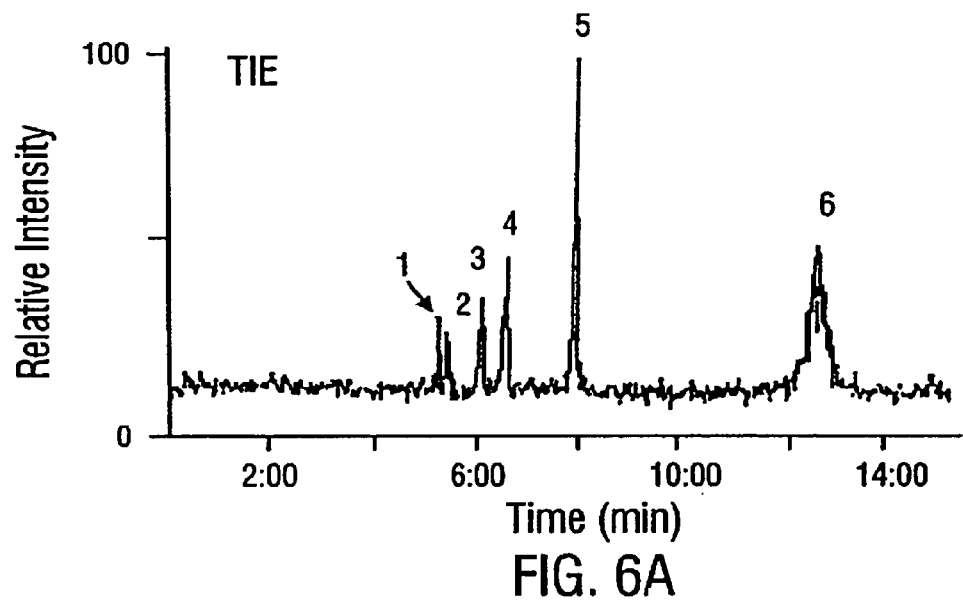
Figure 6B:
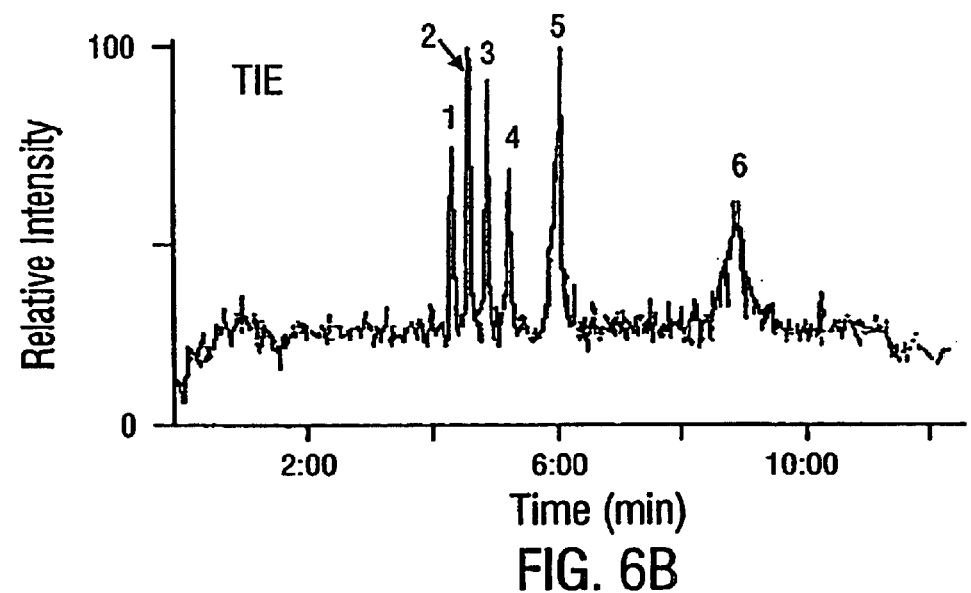
Figure 6C:
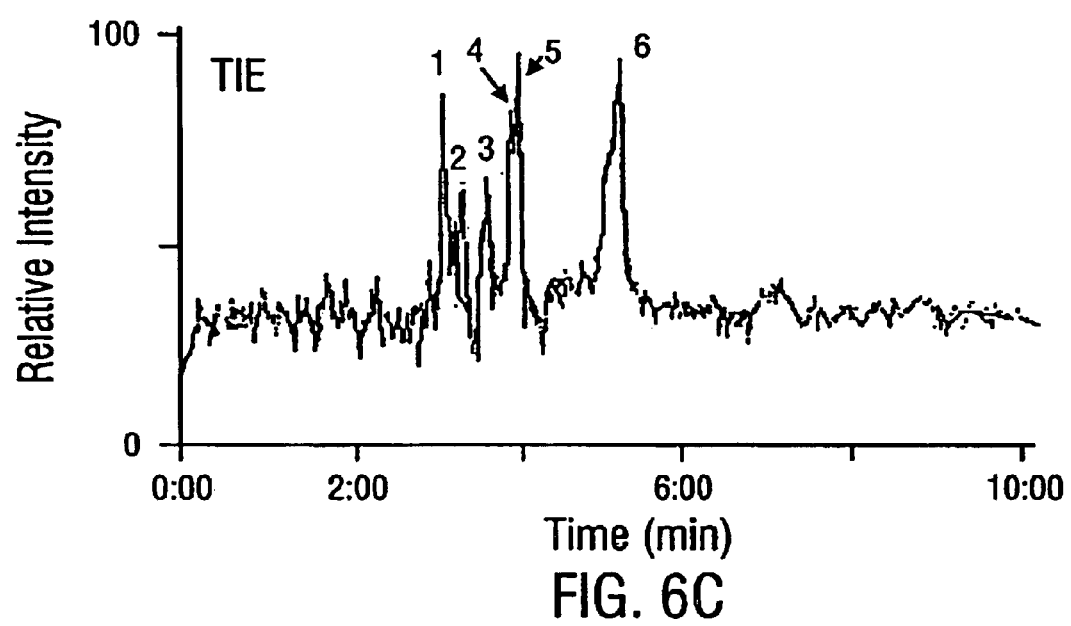
Figure 7A:
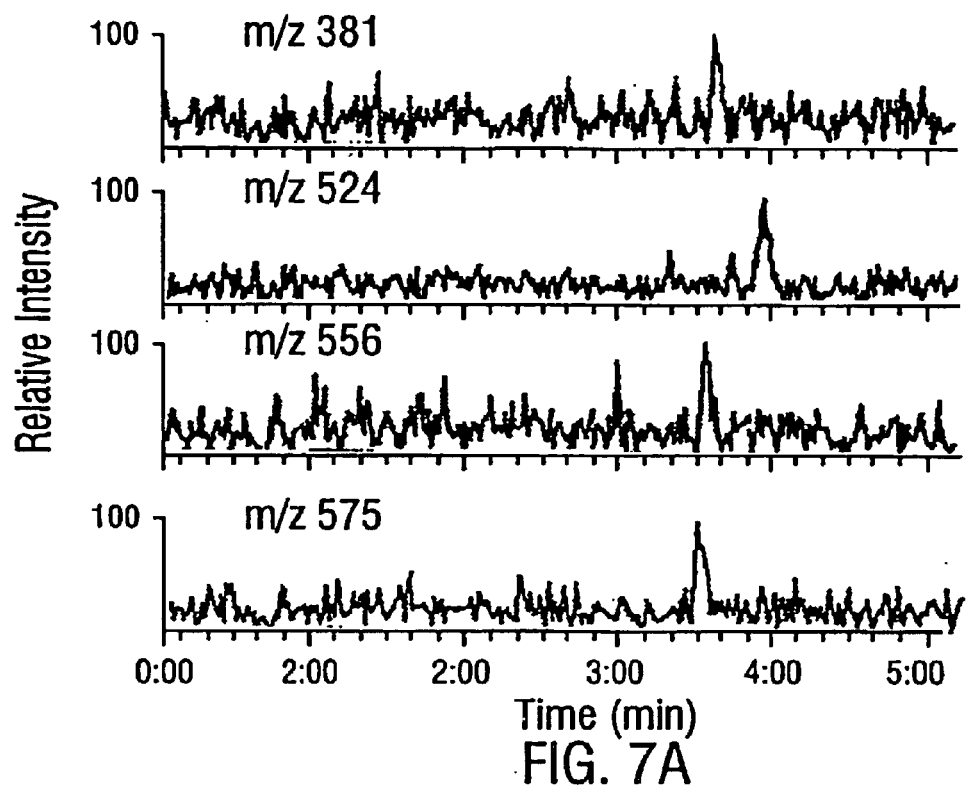
Figure 7B:
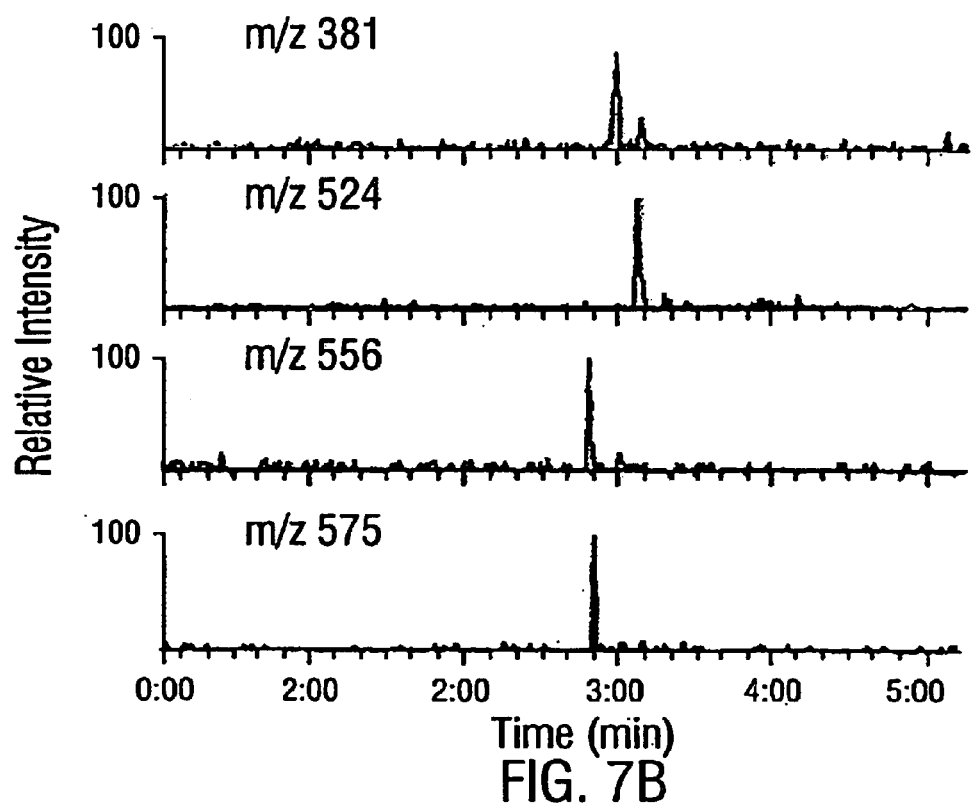
Figure 8:
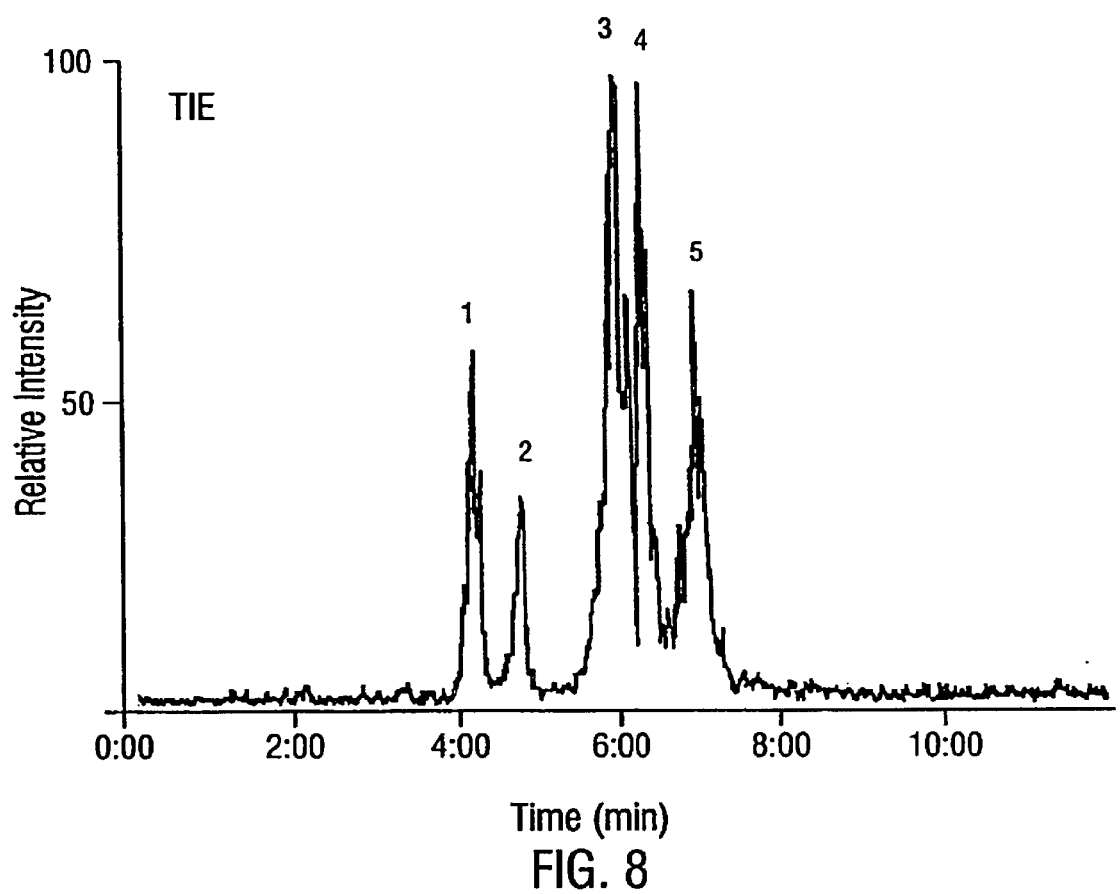
Figure 9A:
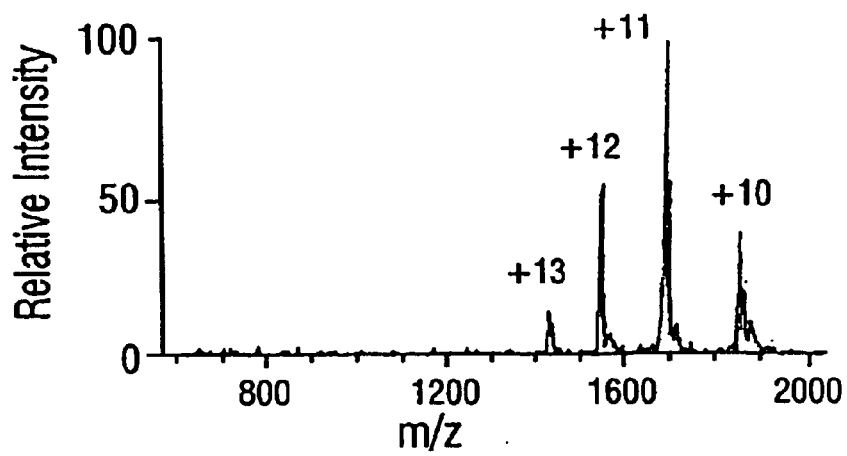
Figure 9B:
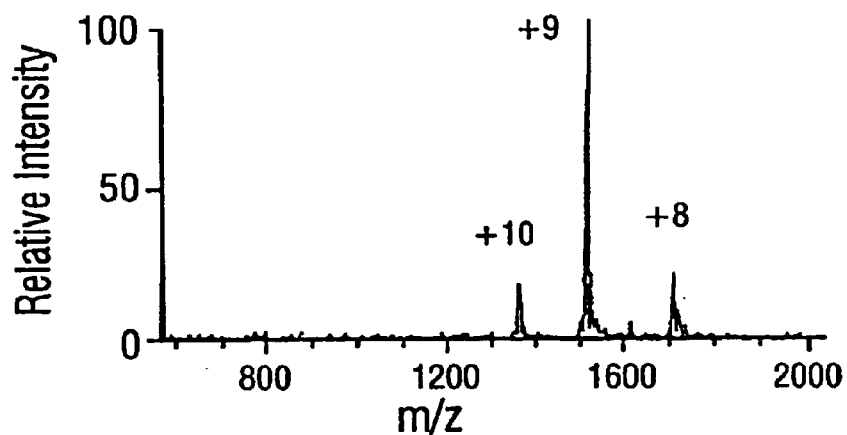
Figure 9C:
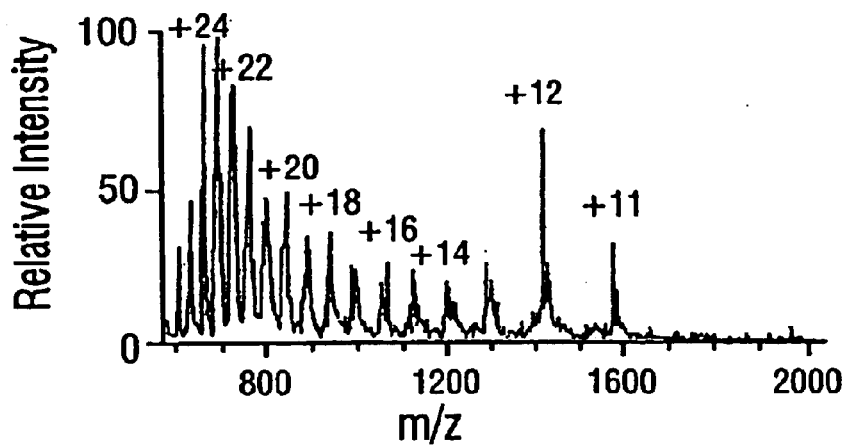
Figure 9D:
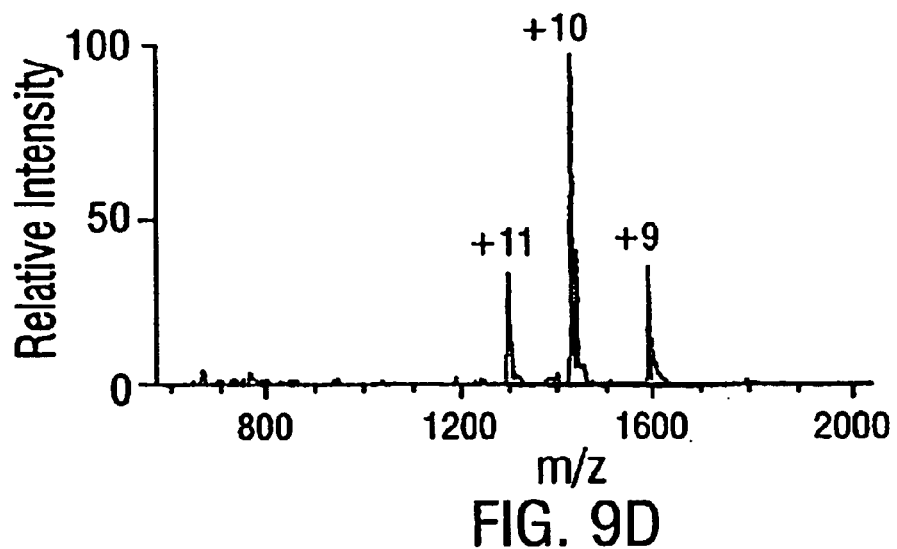
Figure 9E:
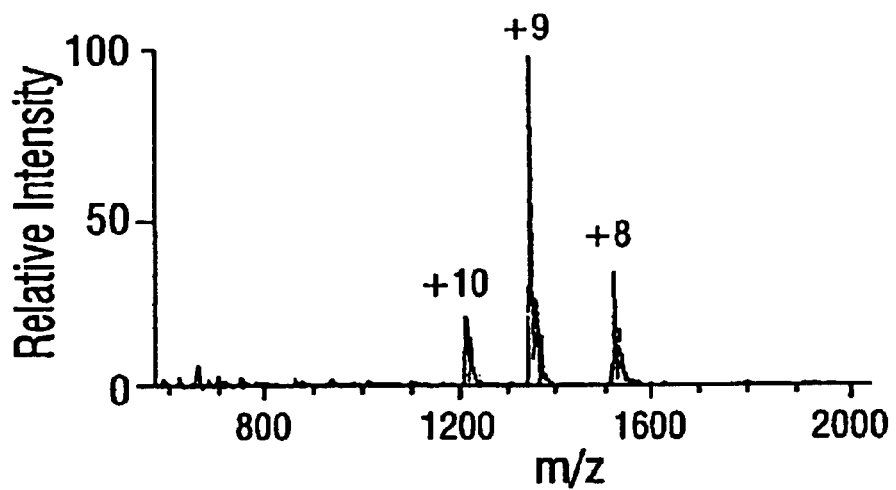
Figure 10A:
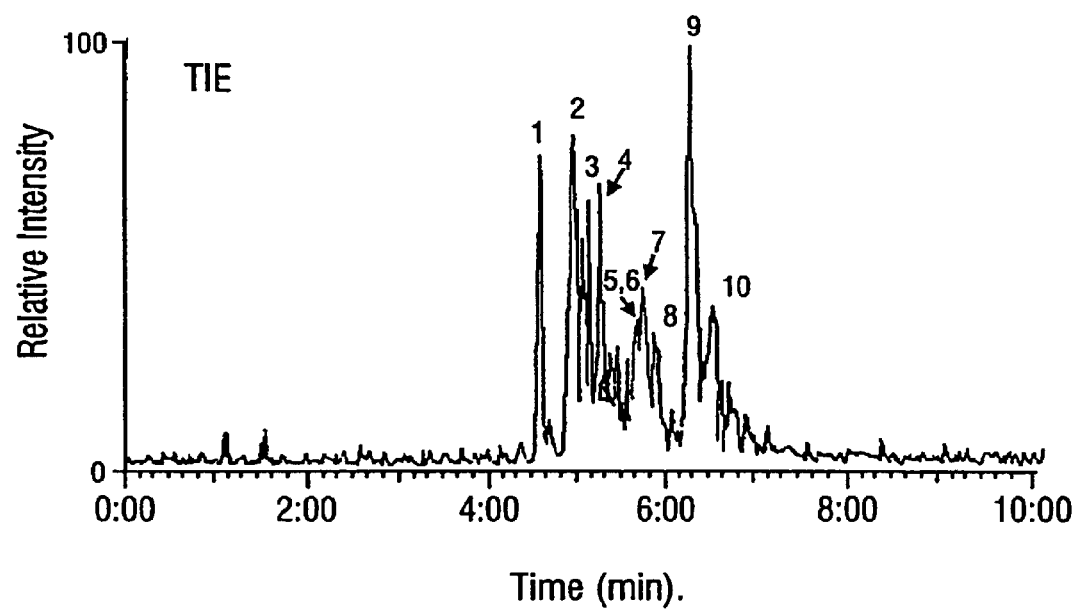
Figure 10B:
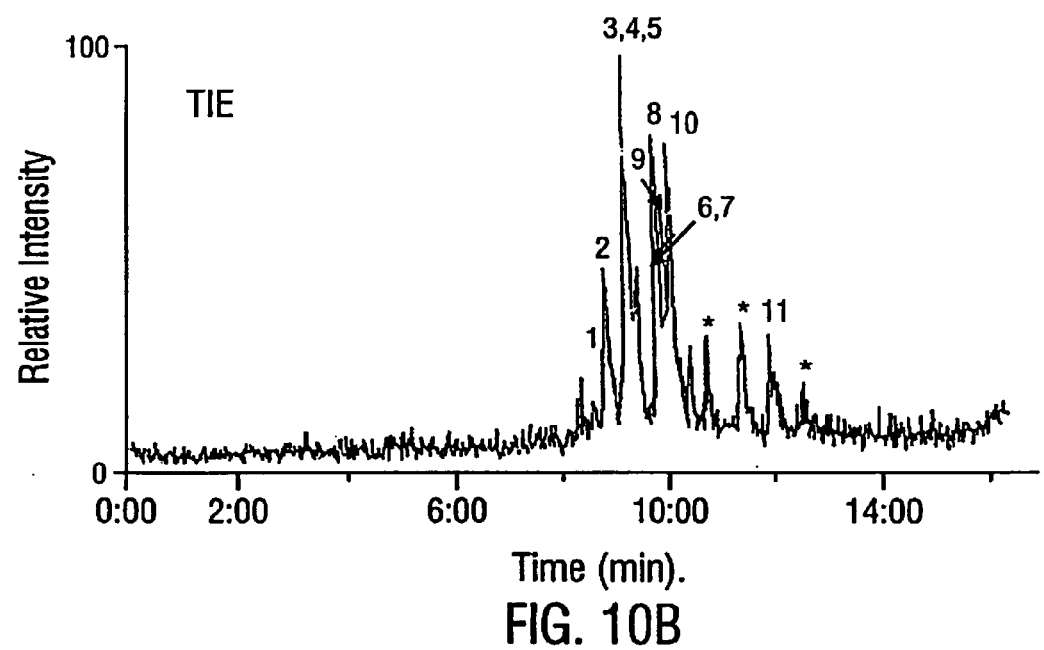
Figure 11A:
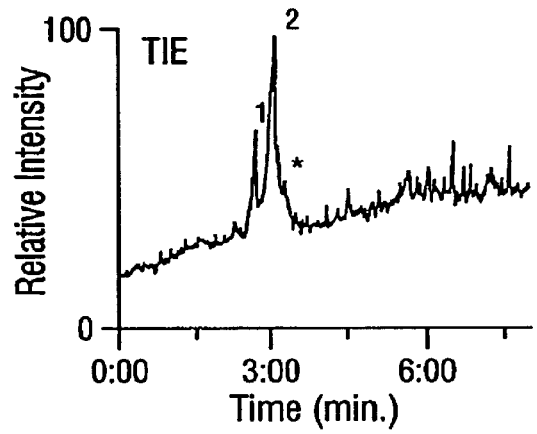
FIG. 11 shows the TIE obtained from the injection of approximately 10 pmol, 1 pmol, 100 fmol, and 10 fmol of the hemoglobin in the human blood samples. As shown, the α (15127 Da) and β (15868 Da) chains of hemoglobin were well separated.
Figure 11B:
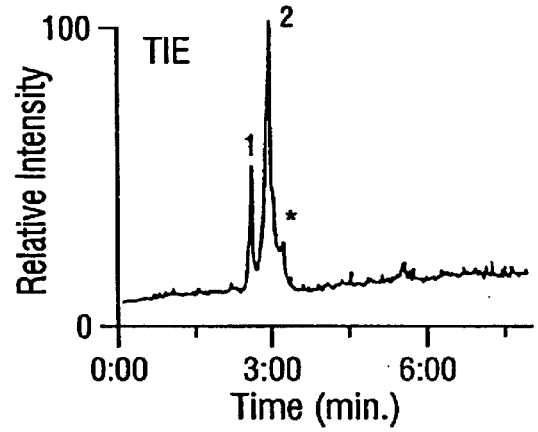
Figure 11C:
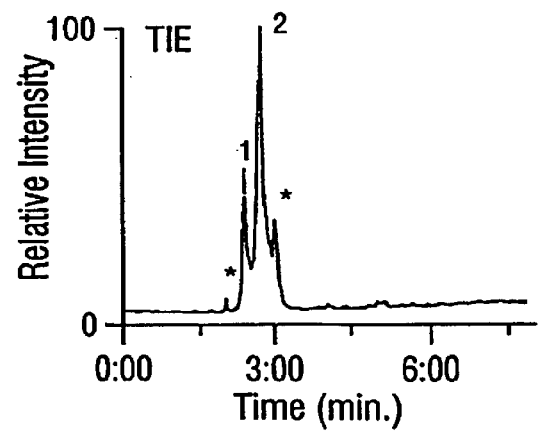
Figure 11D:
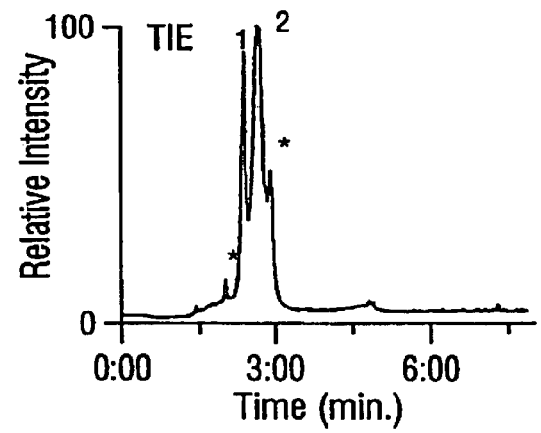
Figure 12A:
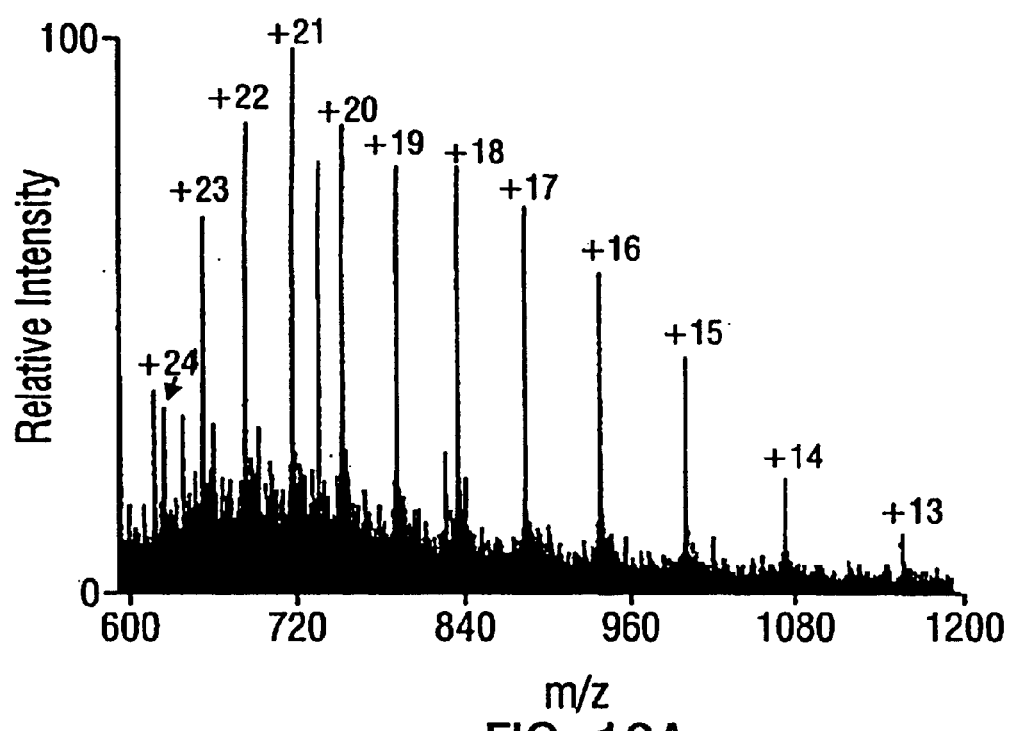
FIG. 12 shows the mass spectra of α and β chains of hemoglobin corresponding to peaks of FIG. 11C. The separation achieved here for α and β chains of hemoglobin are consistent or better than what was reported previously, using CE or CE/MS analysis of hemoglobin of single cells [Hofstadler et al. 1995, Hofstadler et al. 1996].
Figure 12B:
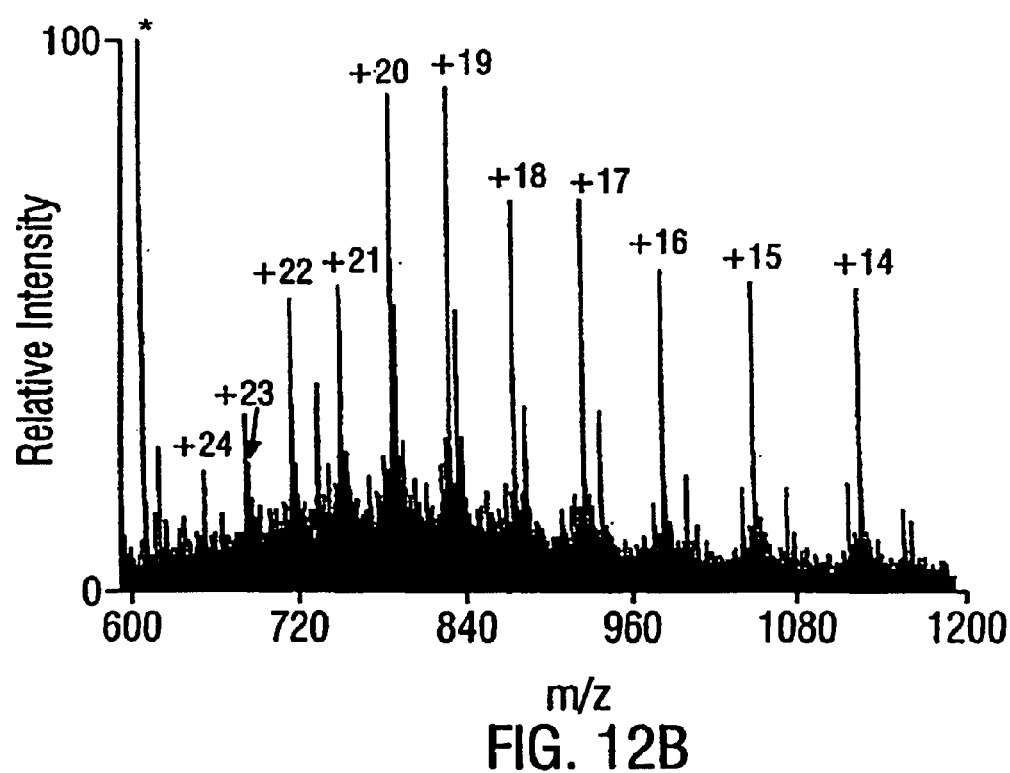

5.7 Example 7
Time-of-Flight Mass Spectrometry for Protein Identification

Mass spectrometry (MS) and tandem mass spectrometry (MS/MS) in conjunction with capillary or micro high performance liquid chromatography (HPLC) or capillary electrophoresis (CE) has recently become a desired technique for peptide mapping. Under capillary HPLC-MS or CE-MS, however, the peak widths resulting from separation are usually very narrow (a few seconds or less). These conditions require mass spectrometers that can acquire data at a rapid rate. Since time-of-flight (TOF) mass spectrometers are capable of acquiring mass spectra at a rate suitable for the analysis of these peaks, they have become the mass spectrometers of choice for HPLC-MS and CE-MS studies.

For the separation of complex biological mixtures, capillary electrophoresis has several advantages over HPLC, including higher resolution capabilities and the ability to analyze smaller sample quantities. As a result, the combination of CE with electrospray ionization (ESI) mass spectrometry has proven to be applicable to a wide range of biologically important mixtures. For example, CE/TOF-MS has been successfully applied to the analysis of standard mixtures of peptides and proteins using amine-coated and bare, fused-silica capillaries in conjunction with the coaxial sheath flow CE technique. While the coaxial sheath flow CE technique is the easiest way to interface CE to MS using electrospray ionization, during the last few years there has been a steady increase in the use of sheathless CE interfaces to mass spectrometry.

Most CE-MS analyses to date have used mass spectrometers which are capable of operating with only unit mass resolution and low mass accuracy. This is because until recently only magnetic sector and FTICR mass spectrometers were capable of generating high resolution, high mass accuracy spectra under electrospray ionization. High resolution, high mass accuracy operation of these instruments, however, usually requires long acquisition times that are incompatible with the narrow peak widths generated by capillary electrophoresis and capillary HPLC.

Recent advances in TOF-MS have made it possible to acquire high resolution (5000, based on the full width of the peak at half its maximum (FWHM)) and high mass accuracy (approximately 10 ppm) data over a wide m/z range (100–3000) on a short time scale (one second or less). These characteristics are especially useful for peptide mapping using capillary HPLC-MS and CE-MS in conjunction with a protein database search.

In order to identify a protein using a protein database, several pieces of information are needed, including the average molecular weight (MW) of the protein and the masses of several peptide fragments obtained through the enzymatic digestion of the protein of interest. The enzymatic digestion of proteins followed by CE-MS or HPLC-MS analyses of their fragments has been routinely used for protein identification using electrospray ionization. However, under ESI conditions, these peptide fragments are often multiply-charged, and to obtain the masses of these multiply-protonated peptides, one must know both the peptides' respective m/z's and charge states. Because the peptide fragments formed under enzymatic digestions, such as tryptic digestion, are usually small (<3000 Da) and their charge states are generally between 1 and 4, a mass spectrometer with a resolving power of approximately 5000 can easily identify the charge states and, therefore, the molecular weights of these peptides.

While knowing the molecular weights of a protein and several of its peptide fragments can greatly enhance the chance of identifying a protein using a protein database, this information may not be sufficient to uniquely identify the protein of interest. This is the case, for example, when dealing with modified proteins and/or when low sample quantities are available, such that the number of peptide fragments that are detectable are too few to unambiguously identify the protein of interest. In these situations, accurate mass measurements of the peptide fragments can be used as yet another important factor to reduce the list of most-likely proteins provided by a protein database and to increase the confidence level of the database search results. In fact, most protein databases allow the user to select error limits associated with the masses of the protonated peptides used in the search, such that higher peptide mass accuracy corresponds to a shorter list of most-likely proteins.

For the analysis of proteins of larger molecular weight, even the additional information about the accurate masses of a few peptide fragments may not be enough to uniquely identify an unknown protein since different peptides may have the same mass. In such cases, tandem mass spectrometry (MS/MS) using in-source fragmentation is a powerful tool for the identification of these peptides based upon the total or partial determination of the amino acid sequences of these peptides. However, since several amino acids differ in mass by 1–2 Da, for more accurate protein identification, it is ultimately desirable to use a mass spectrometer that, in the MS/MS mode, can easily provide the mass accuracy needed to distinguish these amino acids and, therefore, their corresponding peptides from each other.

In this set of examples, the in-capillary electrode sheathless CE/ESI-MS interface of the present invention was utilized to identify horse heart cytochrome c and myoglobin by peptide mapping using high resolution, high mass accuracy TOF-MS. In addition, capillary electrophoresis in conjunction with tandem mass spectrometry using in-source fragmentation was used to determine the amino acid sequences of the peptides formed through the tryptic digestion of horse heart cytochrome c.

5.7.1 Sheathless Interface

An in-capillary electrode sheathless interface according to an embodiment of the present invention was prepared according to the above-disclosed method, using a 10 μm diameter platinum wire for the capillary electrode. An aminopropyl-silane (APS)-treated, 50 μm i.d., 150 μm o.d., 80 cm long CE column (Polymicro Technology, Phoenix, Ariz.) was used in these experiments. In all experiments, the outlet of the CE capillary had been sharpened by immersion in a 50% hydrofluoric acid (HF) solution (Fisher Scientific, Springfield, N.J.) for about 30 minutes while nitrogen gas was passed through the capillary.

5.7.2 Materials

Unless otherwise mentioned, all chemicals were purchased from Sigma Chemical Company (St. Louis, Mo.) and used without further purification. The horse heart cytochrome c and myoglobin were digested following the procedure reported by Takada et al. [1994]. The resulting digest solutions were lyophilized and redissolved in a water+methanol (50/50, v/v) solution containing 3 mM formic acid to obtain a 9 μM final concentration.

Three different experimental solutions were used in these studies. Solution A was prepared by mixing (1:1, v/v) a 40 μM cytochrome c (or 30 μM myoglobin) solution in methanol+water+acetic acid (47:47:6, v/v) with a reference solution containing 1.5 μM L-methionyl-arginyl-phenylalanyl-alanine acetate (MRFA) and 0.05% (v/v) Ultramark 1621 (26, 27) (PCR, Gainesville, Fla.) in methanol+water+acetic acid (49.5:49.5:1, v/v). Solution B was prepared by mixing (1:1, v/v) the previously-mentioned digest solution (of cytochrome c or myoglobin) with the above-mentioned reference solution. Solution C was similar to solution B except that 1.5 μM Ala-gly-ser-glu (AGSE) was used instead of MRFA as a reference compound in order to extend accurate mass measurement to peptides of lower molecular weight.

5.7.3 Equipment

A P/ACE System 2100 (Beckman Instruments, Fullerton, Calif.) CE instrument operating with Beckman System Gold software and a Mariner ESI-TOF mass spectrometer (PerSeptive Biosystems, Inc., Framingham, Mass.) were used for this set of experiments. The mass spectrometer contains a 1 meter reflection time-of-flight mass analyzer which provides a resolving power of 5000 and a mass accuracy of approximately 10 ppm.

Ions are generated in the electrospray ionization chamber and desolvated as they travel through a 25 mm long, 0.4 mm i.d., 6.35 mm o.d. heated capillary (the "nozzle"). After passing through a series of skimmers/orifices to reduce the presence of background neutral gases, the desolvated ions are focused into the ion source push-out chamber, which generates ion pulses at a frequency of 8 kHz. The ions are then extracted from the source and traverse the mass analyzer. Finally, the ions are detected by a microchannel-based detector (Galileo Electro-Optics Corp., Sturbridge, Mass.), and the output signal is measured by a 1 GHz time-to-digital converter.

The mass spectrometer is controlled by a 166 MHz Pentium®-based desktop computer (Micron Electronics, Inc., USA). In this study, the mass spectrometer operated in the mass-to-charge ratio (m/z) range 500–1500 (350–1500 for S/MS) at a rate of 8000 acquisitions/second, which led to the generation of a single spectrum every second. The nozzle temperature was set at 150° C.

5.7.4 Method

A 0.01 M acetic acid running buffer solution (pH 3.4) was used. Between each analysis, the column was washed for 3 minutes with methanol and then for 5 minutes with the running buffer. For analysis of either solution B or solution C, the sample was hydrodynamically injected (1.0 psi, 5 s) into the CE capillary (injecting approximately 1 pmol of each protein digest). A field strength of −398 V/cm was applied to the capillary for separation while a voltage of +1.8 kV was applied to the in-capillary electrode to close the CE electric circuit and to generate the electrospray.

The average molecular weights of the intact proteins were measured by continuous infusion of solution A (containing either cytochrome c or myoglobin) through the CE capillary. The mass deconvolution software of the Mariner was then used to obtain the average molecular weight of each protein from the ESI-MS spectra. Finnigan (San Jose., Calif.) Bioworks software was employed to calculate the exact masses of each peptide and the average masses of the proteins.

For each CE/MS analysis, solution B (containing the reference compounds and either the tryptic digests of cytochrome c or myoglobin) was hydrodynamically injected into the CE inlet. For the accurate mass measurement of each peptide fragment and those for the two reference peaks (m/z 524.266 and m/z 1221.991, designated in FIG. 13 by * and **, respectively) were averaged to obtain a single spectrum. The accurate masses of the reference peaks were then used as internal reference masses for the accurate mass determination of the peptides. This procedure was also used for accurate mass measurements of collisionally-induced peptide fragments except that solution C was used and the instrument operated under in-source fragmentation conditions.

5.7.5 Analysis of Horse Heart Cytochrome c and Myoglobin

Two proteins (horse heart cytochrome c and myoglobin) were used as test compounds. First, the accurate average molecular weights of the two intact proteins were measured as described above using solution A. The measured average molecular weights of horse heart cytochrome c and myoglobin were 12359.2±0.5 Da (calculated mass 12359.80 Da) and 16951.0±0.5 Da (calculated mass 16951.53 Da), respectively. Second, the accurate monoisotopic masses of the peptide fragments derived from the tryptic digestion of cytochrome c and myoglobin were measured by analysis of solution B (containing either cytochrome c or myoglobin tryptic digests) using CE/ESI-MS.

Figure 13A:
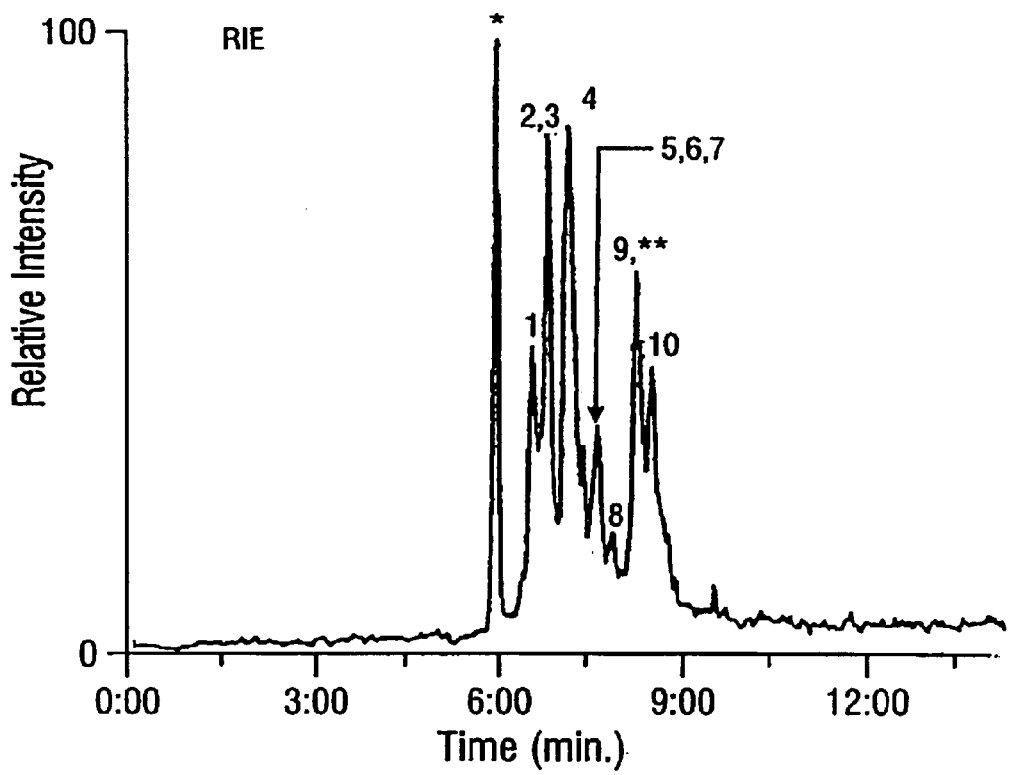
Figure 13B:
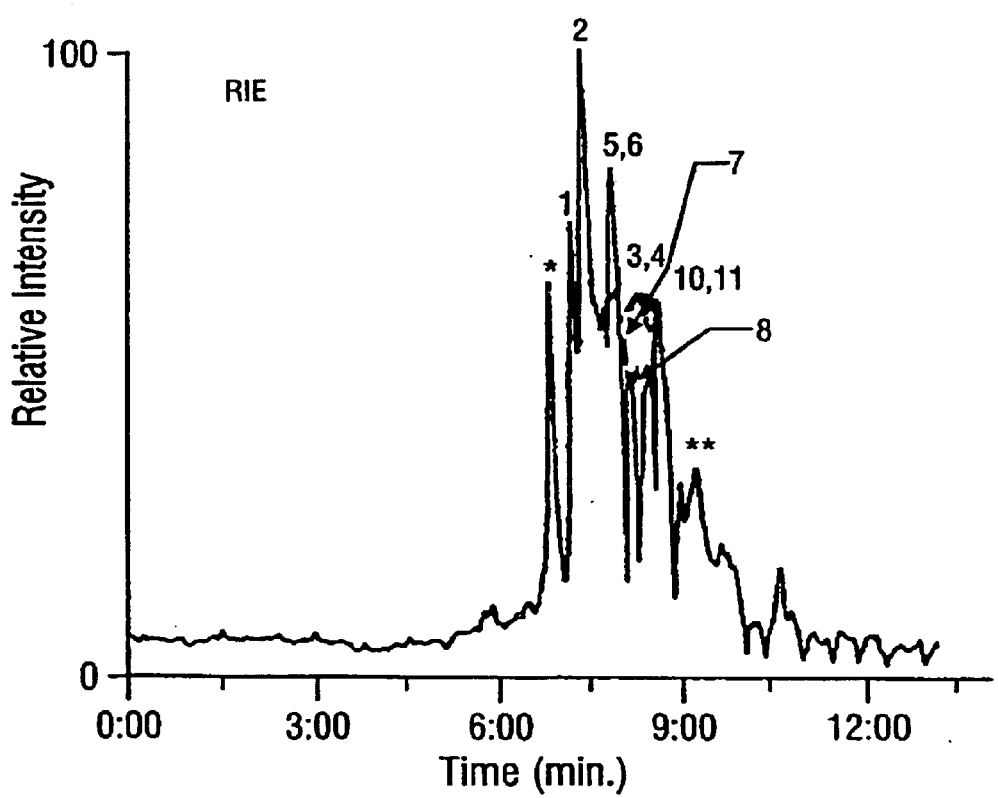

FIGS. 13A and 13B show the reconstructed ion electropherograms (RIE) for the tryptic digests of cytochrome c and myoglobin, respectively. As shown, all tryptic digest fragments of cytochrome c and myoglobin with an m/z in the range of 500–1500 migrated to the CE outlet and were detected within 10 minutes. When two or three peaks overlapped, the m/z of each component was easily identified by analysis of the mass spectrum of the peak.

The results of the accurate mass measurements of the peptide fragments of the two proteins are listed in TABLEs 3 and 4. In most cases, the errors between the calculated and measured masses were less than 10 ppm. Since the experiments were performed at a resolution of 5000, the charge state of each peptide (listed in TABLEs 3 and 4) was easily obtained by inspection of the isotopic spacing that defines the charge state of the peak of interest [Senko et al. 1995].

The following equation provided the accurate mass of each protonated peptide:

$$\{(m/z \times \text{charge state}) - [(\text{charge state} - 1) \times \text{mass of a hydrogen atom, } 1.0078 \text{ Da}]\}$$

The accurate measured masses of the protonated peptide fragments were then used to search the European Molecular Biological Laboratory (EMBL) Protein & Peptide Group database (30) [http://www.mann.emblheidelberg.de/services/peptideSearch/FR_peptidesearch form.html].

To search this database, several inputs are required including protein MW range, digestion enzyme used, measured masses of the protonated peptide fragments, peptide fragment mass accuracy, total number of fragments to be used for the database search, and the number of peptides required to match. Since under the m/z range studied (500–1500) a total of 10 and 11 peaks were observed in these experiments for the cytochrome c and myoglobin digests, respectively, these numbers were used as the total number of peptides to be used for the protein database search, and the default value for the MW of the protein (0–300 kDa) was used. In order to treat these two proteins as "unknowns" and because the accuracy in mass measurements of the instrument is approximately 10 ppm, the mass accuracy was first set to 10 ppm, and the number of peptides required to match was set to 10 and 11 for cytochrome c and myoglobin, respectively.

Under these conditions, the database returned no list for either protein, indicating that the 10 ppm mass accuracy was not valid for all fragments and/or that some peptide fragments were modified or contained impurities. The number of peptides required to match was then decreased by one until it reached a number at which the database was able to provide a list of most-likely proteins.

The maximum values for the number of peptides required to match at which the database was able to return a list were 4 for cytochrome c, and 8 for myoglobin. Under these conditions, the list of most-likely proteins contained only 2 and 4 proteins for cytochrome c and myoglobin, respectively.

Under the same database search conditions but using 1000 ppm mass error, the list of most-likely proteins contained >500 suggestions for cytochrome c and 20 for myoglobin. Setting the maximum number of peptides required to match to 4 or 5 is a realistic case, especially when the sample quantity is very low and only a few peaks are detectable using CE/ESI-MS.

Because the accuracy of the mass spectrometer is around 10 ppm, in the next step, a mass accuracy of 20 ppm was selected for the database search. With this, the maximum number of peptide masses that could be matched increased to 8 peptides for cytochrome c with a single protein match returned by the database. The number of peptide masses that could be matched for myoglobin under these conditions was 11, indicating that all of the fragments' masses had been measured with better than 20 ppm mass accuracy, and the list of most-likely proteins contained 3 proteins. However, the calculated average molecular weight of only one of these three proteins matched the measured average molecular weight of our protein.

Myoglobin represents an easy case in which the protein was unmodified, all peptide fragments were matched in the protein database, and the measured average MW of the protein matched only one of the three proteins suggested by the database with an error of less than 1 Da.

The case for cytochrome c, however, was more complicated and may be more like most real-world analyses because even at 1000 ppm error limit, only 8 out of 10 peaks detected under CE/ESI-MS were matched in the database, indicating that the two other peaks were either impurities or were modified peptides. Moreover, the calculated mass of the most-likely protein was 657.6 Da lower than the measured average mass of the protein of interest. Comparison between the experimentally-determined masses of the two unmatched peptide fragments (TABLE 3, peaks 1 and 10) and the calculated masses of the theoretically-generated fragments of the most-likely protein that had not already been paired with an experimental mass showed that peak number 1 was 42.010 Da greater than the N-terminus fragment of the most-likely protein.

This difference corresponds to a chemical composition of $C_2H_2O$ (42.011 Da), i.e., an acetyl substitution. The mass difference between peak 10 in TABLE 3 (m/z 817.825, doubly-protonated) and the only remaining theoretically-generated fragment of the most-likely protein was 616.197 Da, which was attributed to a heme group (616.198 Da) with a mass accuracy of approximately 1.6 ppm. After adding the molecular weights of these two modifications to the calculated mass of the most-likely protein, the corrected mass difference between the most-likely protein and our measured protein mass was less than 1 Da. The above example clearly shows that the mass accuracy obtained is sufficient to obtain the chemical compositions of the peptides' modifications.

In some cases, however, even knowing the accurate masses of a few peptide fragments may not be enough to uniquely identify a protein because peptides with the same mass could have different amino-acid sequences. Under these conditions, it is desirable to obtain the sequences of these peptides using tandem mass spectrometry. It has been shown that even partial amino acid sequencing can be enough to identify a peptide in a database search with a high confidence level [Mann and Wilm 1994].

To examine the performance of the present CE/ESI-MS system using in-source fragmentation for accurate amino acid sequencing of peptide fragments, the CE/ESI-MS analysis of the tryptic digests of cytochrome c was repeated at an elevated nozzle-skimmer voltage difference. Following CE separation and ionization, the peptide fragments enter the nozzle-skimmer region where they undergo collisionally-induced dissociation (CID).

In this study, in-source fragmentation predominantly produced Y" (carboxyl terminus) fragment ions formed through amide bond cleavage. As before, the accurate masses of the Y" ions of each peptide were measured with respect to internal references (solution C). The results are given in TABLE 5.

As shown in TABLE 5, the maximum error in mass measurement of the Y" ions was approximately 42 ppm. The accurate masses of the amino acids of each peak in this table can be obtained by subtracting the measured masses of adjacent Y" ions. From TABLE 5, it is clear that the mass accuracies associated with Y" ions are well above the accuracies required to identify amino acids which have a 1 or 2 mass unit difference in their molecular weights. The ability to differentiate between these amino acids is especially useful since it increases the confidence level with which a protein identification can be achieved.

Figure 14:
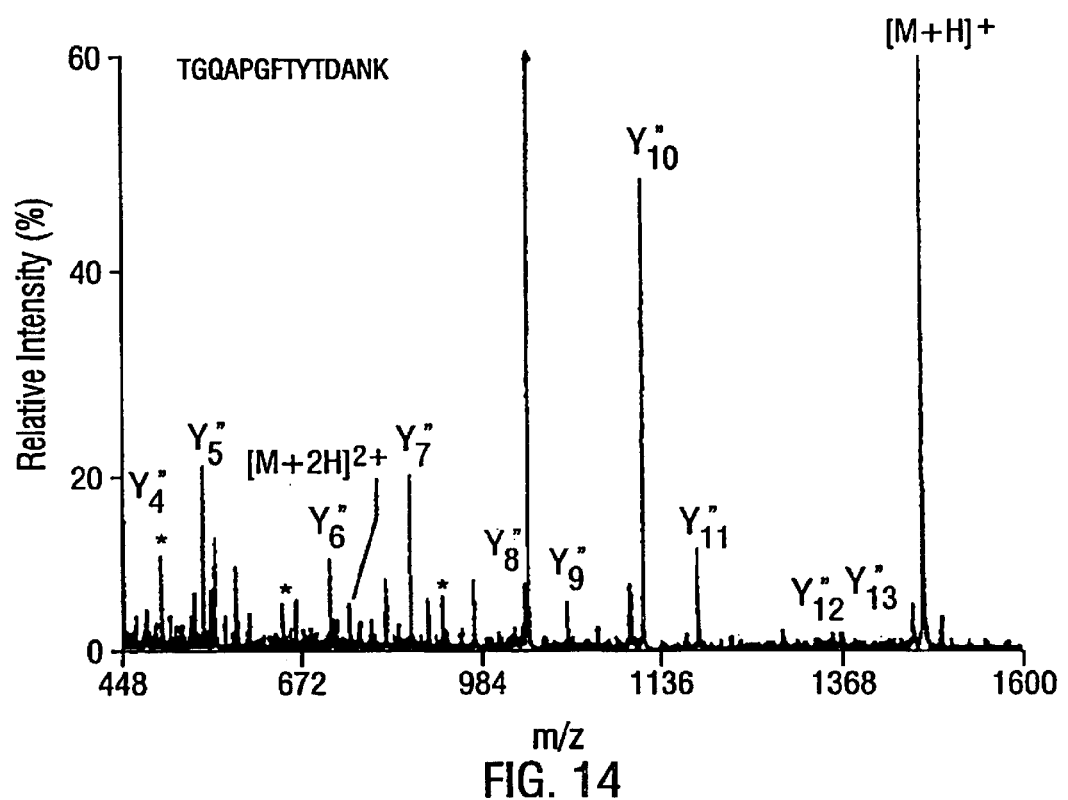

An example of the spectra produced under in-source fragmentation using CE/ESI-tandem MS is shown in FIG. 14, in which peak 3 of FIG. 13A (TGQAPGFTYTDANK, m/z 735.856, doubly-protonated) is collisionally-dissociated. The bold threonine in this fragment is the only amino acid that distinguishes standard horse heart cytochrome c from donkey/zebra cytochrome c, where this threonine is replaced with a serine. The mass difference between Y"$_6$ (measured mass, 711.329 Da) and Y"$_7$ (measured mass, 812.395 Da) fragments identifies a threonine residue (calculated mass, 101.047 Da). Similar results were also obtained for other peaks of FIG. 13A.

5.8 Example 8
Pressure Assisted Capillary Electrophoresis

While CE/ESI-MS has been gaining acceptance for for biological research use, there have been two major obstacles in achieving a routine CE/ESI-MS analysis: (1) lack of a robust CE/ESI-MS interface; and (2) lack of a long-lasting derivatized CE capillary column suitable for the CE/ESI-MS analysis of biological mixtures. The inventors have shown that the robust in-capillary electrode sheathless interface of the present invention may be used for routine CE/ESI-MS analyses of peptides and proteins.

However, under buffer conditions suitable for electrospray ionization (such as 0.01 M acetic acid, pH 3.4), these analyses require derivatization of the inner wall of the fused silica CE columns [Cao and Moini 1997]. This is because at a pH of approximately 3.4 the inner wall of an untreated fused silica capillary column is negatively charged while most peptides and proteins have a net positive charge. The interaction of positively charged peptides and proteins with the negatively charged capillary wall can result in poor separations or even complete analyte loss due to absorption. In addition, due to the low electroosmotic flow (EOF) under these conditions the electrospray process is not stable. Moreover, because of the interaction of analytes with the inner wall of the capillary, analysis time is usually long.

To reduce analyte-wall interaction, several derivatization methods have been introduced to chemically modify the inner wall of the CE capillary for CE/ESI-MS analysis [Hjerten 1985; Cobb et al. 1990; Bruin et al. 1989; Nashabeh et al. 1991; Kohr et al. 1991; Ng et al. 1994; Malik et al. 1993]. One commonly used derivatization technique is the aminopropyl-silane (APS) treatment procedure (12–13) which provides good CE separations and gives stable electrospray currents by producing high EOF of the separation buffer. However, the main disadvantage associated with APS derivatization is that the derivatized columns have a short lifetime of only a few days (2–3 days).

Researchers have used pressure assisted CE (PACE) analysis to solve various CE related problems [U.S. Pat. Nos. 5,482,608 and 5,429,728; Tsuda 1992]. However, the drawback to PACE analysis is that it reduces the CE separation efficiency by converting the flat flow profile of the liquid in the CE column into a parabolic profile [Li 1992]. The resulting decrease in peak resolution may not be acceptable in conventional CE analyses where migration times is used for compound identification. In CE/ESI-MS, however, overlapping peaks can be easily identified based upon their ion electropherograms.

The inventors have determined that the APS derivatized column degrades, the EOF reduces, and a make-up pressure applied to the in-let of CE column is essential to achieve a stable electrospray. In this way, the life expectancy of APS treated columns can be extended greatly.

Hemoglobin is an essential component of human physiology. Abnormalities in hemoglobin can occur as a result of random mutations or as a defense mechanism. It is estimated that 150 million people worldwide carry hemoglobin variants, and many of these variants result in clinical manifestations. Therefore, the structural characterization of hemoglobin is very important for the investigation of molecular evolution and of molecular disease due to abnormal hemoglobin. A number of techniques have been developed over the years to identify and characterize hemoglobin variants. Usually the process of structure characterization of hemoglobin is based on the analysis of tryptic digests of the hemoglobin chains which are separated from blood by means of chromatography. The peptide mapping technique and ion exchange chromatography are the most popular methods of analysis. Recently, HPLC/ESI-MS/MS was used for the analysis of hemoglobin variants [Lee et al. 1991; Covey et al. 1991].

In this set of experiments, the inventors analyze hemoglobin S (HbS), a common hemoglobin variant, using PACE with a degraded APS treated column combined with high resolution, high mass accuracy TOFMS. Intact hemoglobin variants and their tryptic digests were successfully analyzed using CE/ESI-TOFMS. Unequivocal detection of abnormal peptide in the tryptic digest mixture was achieved with tandem mass spectrometry using in-source fragmentation.

5.8.1 Materials

Unless otherwise mentioned, all chemicals were purchased from Sigma Chemical Company (St. Louis, Mo.) and used without further purification. The HbS was digested following the above-disclosed procedure. The digest solution containing a 10.7 $\mu$M concentration of peptides was used without any treatment.

Two different experimental solutions, a peptide mixture (solution A) and a hemoglobin digest solution (solution B) with reference compounds, were used in these studies. Solution A was prepared by dissolving 2 mg of each peptide (Leu-gly, Val-asp, Phe-val, leu-phe, and gramicidin S) in 10 mL of a methanol+water+acetic acid solution (47:47:6, v/v). Solution B was prepared by mixing (1:1, v/v) the previously-mentioned digest solution of HbS with a reference solution containing 1.5 $\mu$M L-methionyl-arginyl-phenylalanyl-alanine acetate (MRFA, MW 524.266) and Ala-gly-ser-glu (AGSE, MW 363.156).

5.8.2 Equipment

An in-capillary electrode sheathless interface was prepared according to the above-disclosed method. Three degraded APS columns (after about 3 days' running) were used in these experiments: two 75 $\mu$m i.d., 150 $\mu$m o.d. capillaries, one 66 cm long and one 110 cm long; and one 30 $\mu$m i.d., 140 $\mu$m o.d. 100 cm long capillary column (Polymicro Technology, Phoenix, Ariz.). In all experiments, the CE capillary outlet tip was sharpened by immersing the tip into a 50% hydrofluoric acid (HF) solution (Fisher Scientific, Springfield, N.J.) for about 30 minutes while $N_2$ gas was passed through it.

The P/ACE System 2100 (Beckman Instruments, Fullerton, Calif.) CE instrument used in this study was capable of simultaneously applying voltage and pressure (0.5 or 20 psi) to the inlet of the CE capillary. However, it did not have pressure programming capabilities, i.e., during separation, the inlet pressure could not be changed continuously from one pressure to another. To achieve this, the instrument's pressure regulator valve was adjusted using a screw attached to a stepping motor (Model SAS P/N 4004–014, Hurst MFG Princeton, Ind.) and stepping motor controller (Model EPC-015, Hurst MFG Princeton, Ind.). Under these conditions, the pressure applied to the CE inlet was adjustable from 0 to 6 psi. It should be understood that alternative means for variably controlling the inlet pressure during separation can also include software, which can be provided by the equipment manufacturer and that the disclosed variable pressure range is in no way limiting. Depending on the means for controlling the inlet pressure during separation, a different set of pressure ranges can be achieved to suit the user's needs.

An electrospray ionization interface used was similar to that disclosed-above. A Finnigan MAT TSQ 70 mass spectrometer (San Jose, Calif.) with an in house fabricated electrospray ionization source was used for the study of the peptide mixtures. The mass spectrometer was operated in single ion monitoring (SIM) mode. For the study of tryptic digests of proteins, a PerSeptive Biosystems Mariner (Framingham, Mass.) electrospray ionization time-of-flight mass spectrometer (ESI-TOFMS) was employed. The mass spectrometer was operated in the m/z range of 200–1500: each data point on the electropherogram represents total of 7500 acquisitions in one second. The nozzle voltage was set at 170V; except that when it was undergoing collisionally-induced dissociation (CID), then it was set at 210V.

Accurate mass measurements and MS/MS were done following the procedure set out in the above-disclosed examples. Briefly, the peaks of the ion electropherogram for each peptide fragment and those two reference peaks (m/z 363.156 and m/z 524.266, designated in FIG. 16 by * and **, respectively) were averaged to obtain a single spectrum. The accurate masses of the reference peaks were then used as internal reference masses for the accurate mass determination of the peptide. This procedure was also applied to the accurate mass measurements of CID peptide fragments which the instrument operated under in-source fragmentation condition.

5.8.3 Pressure Programming CE/ESI-MS

To demonstrate the utility of pressure programming at the CE inlet, a mixture containing Leu-gly, Val-asp, Phe-val, Leu-phe, and gramicidin S was studied. FIG. 15 shows the CE/ESI-MS selected ion electropherograms of the mixture's components under different pressure programs using selected ion monitoring mode. For these experiments, five masses were selected using a dwell time of 0.2 seconds for each mass. In addition, the 110-cm-long degraded APS capillary column was used for a better separation. Approximately the same amount of sample (1 μpmol each peptide) was hydrodynamically injected each time (1.0 psi for 5 seconds). A separation voltage of −30 kV was applied to the inlet, and +2.4 kV was applied to the electrospray electrode for these experiments.

Figure 15A:
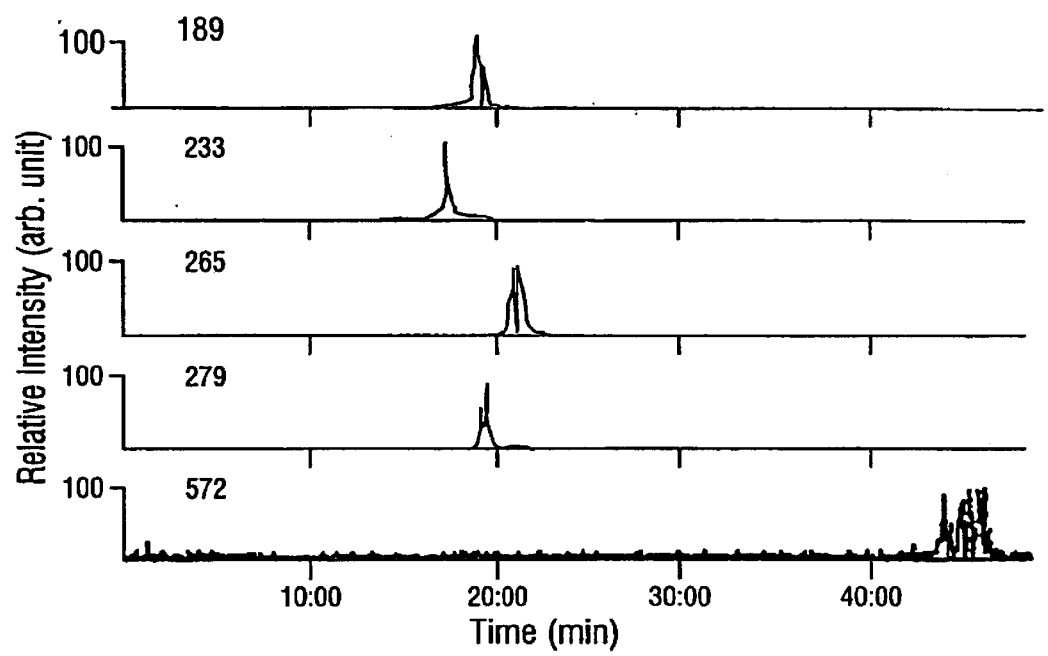

FIG. 15A shows the results obtained when 0.5 psi pressure was applied to the inlet throughout the separation. Under these conditions, the total analysis time was about 50 minutes. The peak of gramicidin S (m/z 572), the last peak of the reconstructed ion electropherogram (RIE), was very wide due to the stronger interaction of gramicidin S with the capillary's inner wall.

Figure 15B:
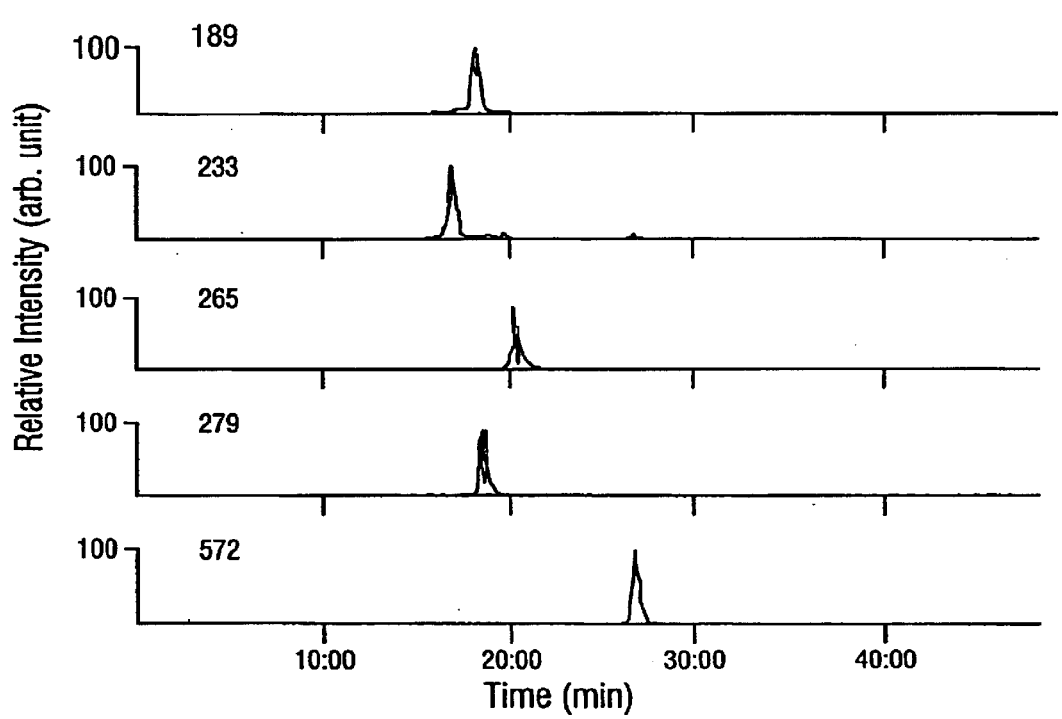

In FIG. 15B the applied pressure was maintained at 0.5 psi for the first 22 minutes. After the four dipeptides eluted from the column, the inlet pressure was ramped to a final pressure of 3.8 psi at a rate of 0.6 psi/min, reducing the total analysis time to less than 30 minutes. In addition, the higher pressure enhanced the signal-to-noise ratio (S/N) of the gramicidin S peak by decreasing its peak width.

Figure 15C:
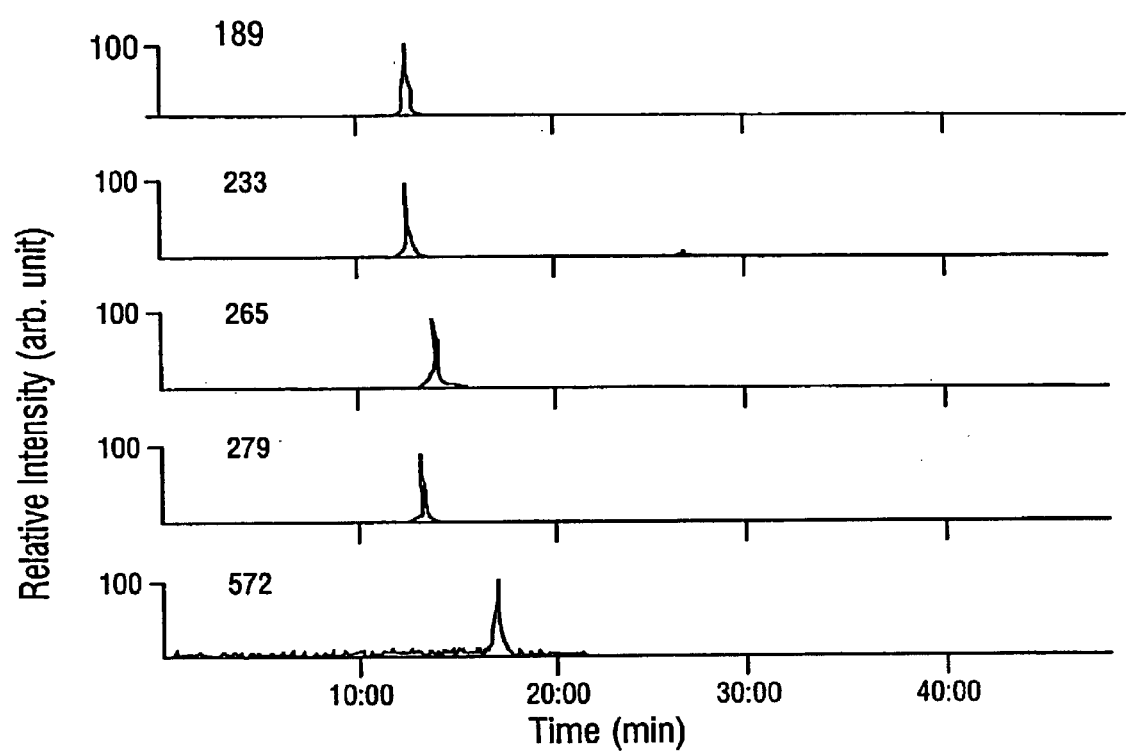

In FIG. 15C, the pressure programming was modified as follows to further reduce the analysis time: 1) for the first 6 minutes, the pressure was increased from 0 to 2.0 psi at a rate of 0.33 psi/min; 2) the pressure was maintained at 2.0 psi for 9 minutes until all four dipeptides eluted from the column; and 3) the pressure was then ramped to 4.0 psi at a rate of 0.72 psi/min and kept at 4.0 psi throughout the remainder of the experiment. As shown in FIG. 15C, the analysis time was further reduced to about 18 minutes.

5.8.4 Analysis of Tryptic Digests of Hb

The great majority of the known hemoglobin variants differ from their normal counterparts only by having an amino acid substitution at a single position in one pair of chains. HbS arises from the substitution of a hydrophobic valine residue for the hydrophilic surface residue glutamic acid. Therefore, the tryptic digested normal hemoglobin (HbA) and HbS differ in the peptides constitute the eight N-terminal residues of the β-subunit of Hb. Their amino acid sequence are:

HbA Val-His-Leu-Thr-Pro-Glu-Glu-Lys MW 951.503 Da

HbS Val-His-Leu-Thr-Pro-Val-Glu-Lys MW 921.528 Da

Figure 16:
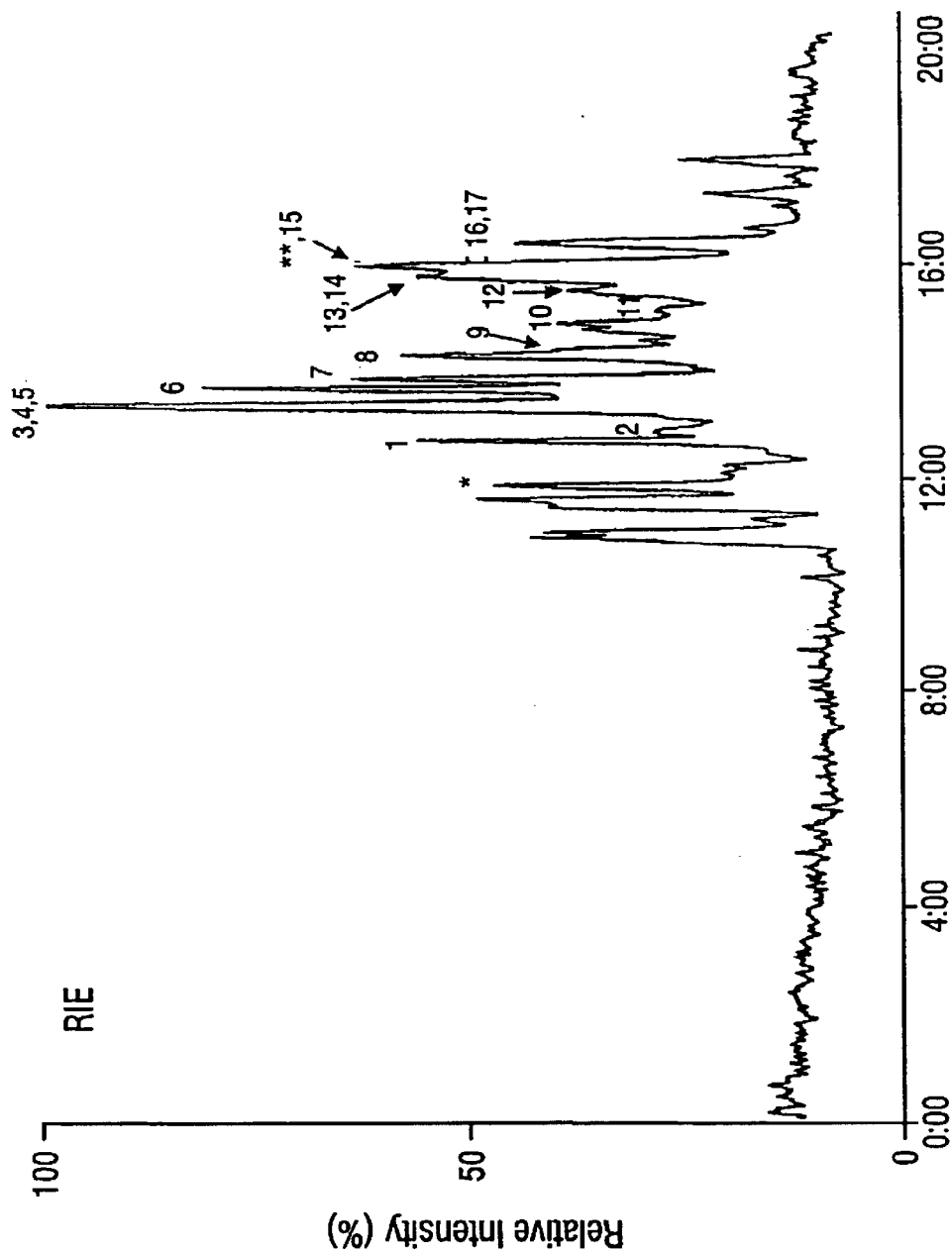

FIG. 16 shows the total ion electropherogram (TIE) for the tryptic digests of HbS using CE/ESI-TOFMS. A 30 μm i.d. 100 cm long degraded APS column was employed for this study. The CE was operated under −200 V/cm field strength with 3.5 psi back pressure applied at the capillary inlet. Approximately 200 fmol of each peptide was injected into CE column.

As shown, most of the tryptic digest fragments of HbS with an m/z in the range of 350–1000 migrated to CE outlet and were detected. When two or three peaks overlapped, the m/z of each component was easily identified by analysis of the mass spectrum of the peak. The results of the accurate mass measurements of the peptide fragments of the HbS are listed in TABLE 6. In most cases, the error between the calculated and measured masses were less than 10 ppm.

Figure 17:
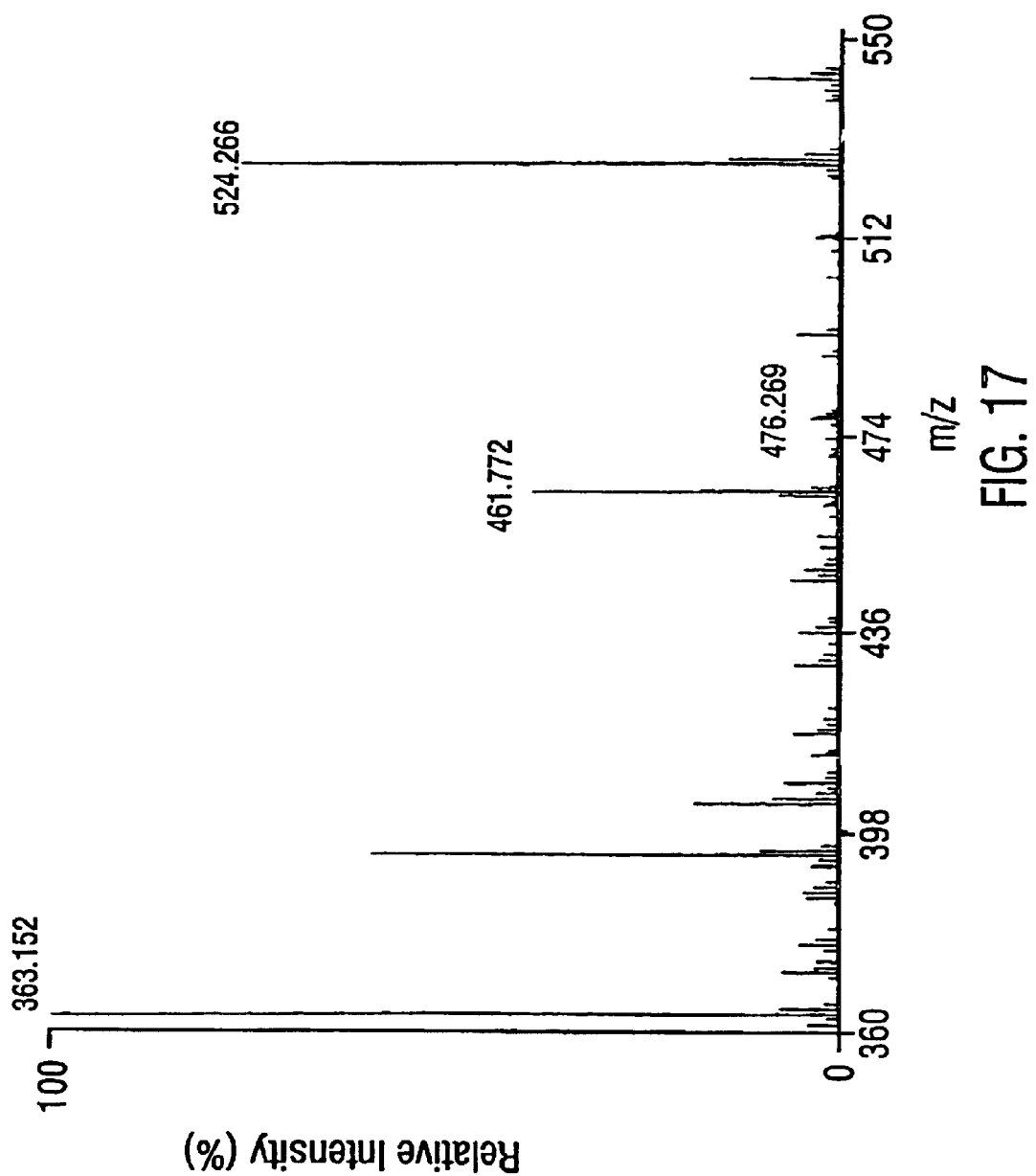

FIG. 17 shows the calibrated mass spectra of the peak 16 of FIG. 16 which corresponds to the eight N-terminal residue peptide of HbS. The error is less than 1 ppm. From the spectra, approximately 20% of the eight N-terminal residue peptide of HbA was also detected and the mass error was less than 10 ppm which indicated that there were about 80% HbS and 20% HbA in the original HbS sample. This result was further confirmed by the direct infuse analysis of the intact HbS.

In order to increase the confidence level associated with this identification, on-line in-source fragmentation of the peptide of interest (VHLTPVEK, the eight N-terminal residue peptide of HbS) was carried out to obtain accurate amino acid sequence. The CE/ESI-TOFMS analysis of the tryptic digests of HbS was repeated at an elevated nozzle-skimmer voltage difference. Following CE separation and ionization, the peptide fragments enter the nozzle-skimmer region where they undergo CID.

Figure 18:
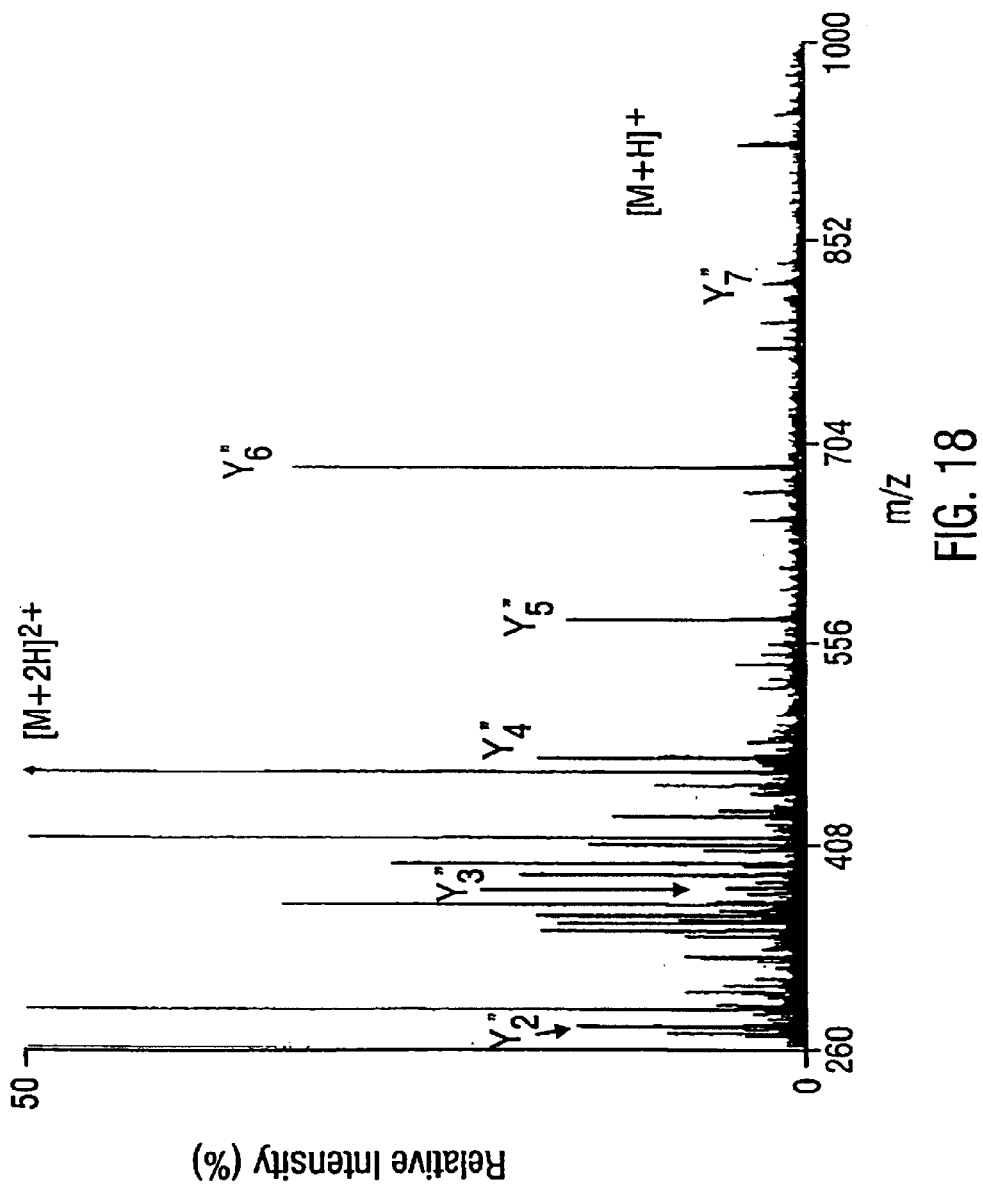

The mass spectra of the eight N-terminal residue peptide of HbS produced under MS/MS is shown in FIG. 18 which corresponds to the peak 16 in FIG. 16. As before, the in-source fragmentation predominantly produced Y" (carboxyl terminus) fragments formed through amide bond cleavage. The mass error for each fragment was less than 30 ppm. The mass differences between $Y"_6$ (measured mass, 375.219 Da) and $Y"_7$ (measured mass, 276.163 Da) fragments identifies a valine residue (calculated mass, 99.068 Da and measured mass 99.056 Da, mass error 121 ppm). This mass accuracy is sufficient to identify valine from any other amino acids.

A detection limit for the eight N-terminal residue peptide of HbS was approximately 10 fmol under the experiment conditions used.

6.0 CONCLUSION

The foregoing description and illustrations contained herein demonstrate many of the advantages associated with the present invention. In particular, it has been revealed that the in-capillary electrode sheathless interface was successfully applied to the CE/ESI-MS analysis of mixtures of small peptides, proteins, and tryptic digests of proteins. Experimental variables relevant to this design, including the distance of the in-capillary electrode from the CE outlet and the length of the electrode inside the capillary, had no significant effect on the CE separation. However, significant enhancement of the sensitivity resulted from the use of a narrow CE capillary. A detection limit of 600 attomoles of myoglobin was achieved under wide scan m/z range of 500–1500 using a 30 μm i.d., APS-treated capillary. Under multiple-ion monitoring mode and using a 50 μm i.d. APS-treated capillary, a detection limit of 100 attomoles was achieved for cytochrome c and myoglobin. Major tryptic fragments of cytochrome c and myoglobin were identified in less than 10 minutes and by consuming only several nanoliters of sample. The interface was capable of separating and detecting the major protein components of whole blood (α and β hemoglobin) at 10 femtomole levels with ease.

The resulted presented herein also demonstrate that a combination of (1) ESI-MS analysis of the intact protein, (2) CE/ESI-MS analysis of the tryptic digests of the protein using high mass accuracy, high resolution time-of-flight mass spectrometry, and (3) CE/ESI-high resolution, high mass accuracy tandem mass spectrometry analysis of peptide fragments can uniquely characterize and verify the identity of a protein of interest.

Furthermore, the results presented herein demonstrate that a combination of (1) ESI-MS analysis of the intact protein; (2) CE/ESI-MS analysis of the tryptic digests of the protein using high mass accuracy, high resolution time-of-flight mass spectrometry; and (3) CE/ESI-high resolution, high mass accuracy tandem mass spectrometry analysis of peptide fragments can uniquely characterize and verify the identity of a protein of interest.

Additionally, PACE technique was used to extend the life expectancy of APS treated columns. A common hemoglobin variant (HbS) was analyzed using PACE/ESI-high resolution, high mass accuracy TOF-MS. The results show that unequivocal detection of abnormal peptide in the tryptic digest mixture of HbS was achieved with tandem mass spectrometry using in-source fragmentation.

Thus, it is apparent that there has been provided, in accordance with the invention, a novel sheathless interface for capillary electrophoresis/electrospray ionization-mass spectrometry using an in-capillary electrode that substantially meets the need and advantages set forth previously. Although the invention has been described and illustrated with reference to specific embodiments thereof, it is not intended that the invention be limited to these illustrative embodiments. Those skilled in the art will recognize that modifications and variations can be made without departing from the spirit of the invention. For example, platinum wire is in no way the only available material that can be used for the electrode. Any conductive filament that is suitably conductive and inert to chemicals—such as, for example, gold—may be used. Additionally, while epoxy was mentioned as the means for sealing the hole in the capillary and securing the electrode thereto, other means may be employed, such as glass seals, glass-to-metal seals. Furthermore, chemical modification of the capillary column is in no way limited to APS derivatization. Other chemical modifications are envisioned to be within the spirit of the invention. Moreover, a sheathless interface having an in-capillary electrode according to the present invention is in no way limited to a single electrode. Multiple holes along the length of the capillary column may be formed in the capillary column wall so that multiple electrodes may be inserted. Additionally, the capillary column may have multiple outlet ends. One way to achieve this is to make a capillary column that splits into multiple legs—e.g., Y-shape, T-shape, football goal-shape, etc.—wherein each outlet end would have its own in-capillary electrode.

It is also important to note that practice of the pressure assisted capillary electrophoresis aspect of the present invention is not limited in any way to in-capillary electrode. The pressure assisted method wherein the inlet pressure is ramped during separation may also be practiced with any type of capillary, whether or not it is chemically modified, degraded, has an in-capillary electrode, or has some other form of electrode. One should also note that in practicing the invention, one is not limited to buffer solutions of any particular pH level. Although acidic buffer solutions were used in the experiments, it is envisioned that neutral and basic buffer solutions may also be used for certain applications.

Moreover, the application of the in-capillary electrode is not limited to capillary electrophoresis. For example, the in-capillary electrode can be used as an interface between high performance liquid chromatography and mass spectrometry. Alternatively, it can also be used as a means of providing electrical potential to nanospray tips. Therefore, it is intended that this invention encompass all such variations and modifications falling within the scope of the appended claims.

6.0 REFERENCES

The following references, to the extent that they provide exemplary procedural or other details supplementary to those set forth herein, are specifically incorporated herein by reference.

1. A non-redundant database is maintained by C. Sanders at EMBL and can be accessed via the internet at http://www.mann.embl-heidelberg.de/services/peptideSearch/FR_peptidesearchform.html
2. Bank, J. F. and Dresch, T., *Anal. Chem.* 68:1480, 1996.
3. Banks, J. F. and Gulcicek, E. E., *Anal. Chem.* 69:3973, 1997.
4. Banks, J. F., *J. Chromatogr. A*, 712:245, 1995.
5. Bruin, G. J. M.; Chang, J. P.; Kuhlman, R. H.; Zegers, K.; Kraak, J. C.; and Poppe, H., *J. Chromatogr.*, 471:429, 1989.
6. Bunn, H. F.; Forget, B. G., *Hemoglobin: Molecular, Genetic and Clinical Aspects*, W. B. Saunders, Philadelphia, 1986.
7. Bunn, H. F.; Forget, B. G.; Ranney, H. M., *Human Hemoglobins* W. B. Saunders, Philadelphia (1977).
8. Cai, J.; Henion, J. *J. Chromatogr.*, 703:667, 1995.
9. Cao, P. and Moini, M., *J. Am. Soc. Mass Spectrom.*, 8:561, 1997.
10. Cao, P.; Moini, M. *Proceedings of the 43rd ASMS Conference on Mass Spectrometry and Allied Topics*, Atlanta, GA, 21 May 1995.
11. Cao, P.; Moini, M., *J. Am. Soc. Mass Spectrom.*, 8:561, 1997.
12. Carr, S. A.; Hemling, M. E.; Bean, M. F. and Robert, G. D., *Anal. Chem.*, 63:2802, 1991.
13. Cedric; Shackleton, H. L.; Ewa, H.; Witkowska, *Anal. Chem.* 29A, 1996.
14. Chen, H. and Horvath, C., *J. Chromatogr.*, 705:3, 1995.
15. Cobb, K. A.; Dolnik, V.; and Novotny, M., *Anal. Chem.*, 62:2478, 1990.
16. Covey, T. R.; Huang, E. C.; Henion, J. D., *Anal. Chem.* 63:1193, 1991.
17. *Electrospray Ionization Mass Spectrometry: Fundamentals, Instrumentation & Applications*, John Wiley & Sons, Inc., New York, Chapters 6 and 8, 1997.
18. Fang, L.; Zhang, R.; Williams, E. R.; Zare, R. N. *Anal. Chem.* 66:3696, 1994.
19. Figeys, D.; Oostveen, I. V.; Ducret, A.; Aebersold, R. *Anal. Chem.* 68:1822, 1996.
20. Foret, F.; Thompson, T. J.; Vouros, P.; Karger, B. L. *Anal. Chem.* 66:4450, 1994.

21. Gale, D. C.; Smith, R. D. *Rapid Commun. Mass Spectrom.* 7:1017, 1993.
22. *Handbook of Capillary Electrophoresis Applications*, Shintani, H. and Polonsky, J,. Chapman & Hall, New York, 1997, Chapter 11.
23. Hjerten, S., *J. Chromatogr.*, 347:191, 1985.
24. Hofstadler, S. A.; Severs, J. C.; Smith, R. D.; Swanek, F. D.; Ewing, A. G., *Rapid Commun. Mass Spectrom.*, 10:919, 1996.
25. Hofstadler, S. A.; Swanek, F. D.; Gale, D. C.; Ewing, A. G.; Smith, R. D., *Anal. Chem.*, 57:1477, 1995.
26. Houston, C. T.; Reilly, J. P., *Rapid Commun. Mass Spectrom.*, 11: 1435, 1997.
27. Jackett, J.; Moini, M. *Rev. Sci. Instrum.* 65:591, 1994.
28. Jiang, L. and Moini, M., *J. Am. Soc. Mass Spectrom.*, 3:842, 1992.
29. Jiang, L. F.; Moini, M., *J. Am. Soc. Mass Spectrom.*, 6:1256, 1995.
30. Joanne, C. S.; Amy, C. H. and Smith, R. D., *Rapid Commun. Mass Spectrom.*, 10:1175, 1996.
31. Joregenson, J .W. and Lukacs, K. D. *Science*, 222:266, 1983.
32. Kriger, M. S.; Cook, K. D.; Ramsey, R. S. *Anal. Chem.* 67:385, 1995.
33. Kohr, J. and Engelhart, H., *J. Microcol. Sep.*, 3:491, 1991.
34. Landers, J. P., Ed. *Handbook of Capillary Electrophoresis*; 2d Ed.: CRC: Boca Raton, FL., p.35, 1997.
35. Lapolla, A.; Fedele, D.; Aronica, R.; Garbeglio, M.; D'Alpaos. M.; Plebani, M.; Seraglia, R.; Traldi, P., *Rapid Commun. Mass Spectrom.*, 11:613, 1997.
36. Lazar, I. M.; Xin, B.; Lee, M. L.; Lee, E. D.; Rockwood, A. L.; Fabbi, J. C. and Lee, H. G.,*Anal. Chem.*, 69:3205, 1997.
37. Lee, E. D.; Muck, W.; Henion, J. D.; Covey, T. R. *Biomed. Env. Mass Spectrom.*, 18: 844, 1989.
38. Lee, T. D.; Rahbar, S.,*In Mass Spectrometry of Peptides*; Desiderio. D. M., Ed.; CRC: Boca Raton, FL, p. 257, 1991.
39. Li, L.; Golding, R. E.; Whittal, R. M.,*J. Am. Soc. Mass Spectrom.*, 118:11662, 1996.
40. Li, S. F. Y., Capillary electrophoresis, *Elsevier Science Publishers* B.V. p. 15, 1992.
41. Malik, A.; Zhao, Z.; and Lee, M. L.,*J. Microcol., Sep.*, 5:119, 1993.
42. Mann, M. and Wilm, M., *Anal. Chem.*, 66:4390, 1994.
43. Mesaros, J. M.; Ewing, A. G.; Gavin, P. F., *Anal. Chem.* 1994, 66, 527A.
44. Moini, M., *Rapid Commun. Mass Spectrom.*, 8: 711, 1994.
45. Moseley, M. A.; Jorgenson, J. W.; Shabanowitz, J.; Hunt, D. F.: Tomer, K. B. *J. Am. Soc. Mass Spectrom.* 3:289, 1992.
46. Muddiman, D. C.; Rockwood, A. L.; Gao, Q.; Severs, J. C.; Udseth, H. R. and Smith, R. D.,*Anal. Chem.*, 67:4371, 1995.
47. Nashabeh, W. and Rassi, Z. E. I., *J. Chromatogr.*, 559:367, 1991.
48. Ng, C. L.; Lee, H. K.; and Li, S. R. Y., *J. Chromatogr.*, 659:427, 1994.
49. Olivares, J. A; Nguyen, N. T.; Yongker, C. R.; Smith, R. D. *Anal. Chem.* 59:1230, 1987.
50. Roberts, G. D.; Johnson, W. P.; Burman, S.; Anumula, K. R. and Carr, S. A., *Anal. Chem.*, 67:3613, 1995.
51. Roepstorff, P. and Fohlman, J., *Biomed Mass Spectrom.*, 11:601, 1984.
52. Senko, M. W.; Beu, F. W. and McLafferty, F. W.,*J. Am. Soc. Mass Spectrom.*, 6:229, 1995.
53. Severs, J. C.; Harms, A. C.; Smith, R. D. *Rapid Commun. Mass Spectrom.* 10:1175, 1996.
54. Smith, R. D.; Barinaga, C. J.; Udseth, H. R. *Anal. Chem.* 60:1948, 1988.
55. Smith, R. D.; Loo, J. A.; Loo, R. R. O.; Busman, M.; Udseth, H. R. *Mass Spectrom. Rev.* 10:359, 1991.
56. Takach, E. J.; Peltier, J.; Gabeler, S.; Verentchikov, A.; Vestal, M. L. and Martin, S. A. Presented at The Association of Biomolecular Resource Facilities International Symposium, Feb, 1997 (ABRF'97).
57. Takada, Y.; Nakayama, K.; Yoshida, M.; Sakairi, M., *Rapid Commun. Mass Spectrom*, 8:695, 1994.
58. Thompson, T. J.; Foret, F.; Kirby, D. P.; Vouros, P.; Karger. B. L. Presented at the 41st ASMS Conference on Mass Spectrometry and Allied Topics, San Franciso, CA, 31 May 1993.
59. Tsuda, T., LCGC, 5:32, 1992.
60. U.S. Pat. No. 5,482,608.
61. U.S. Pat. No. 5,429,728.
62. Valaskovic, G. A.; Kelleher, N. L.; McLafferty, F. W. *Science*, 273:1199, 1996.
63. Wada, Y.; Matsuo, T.; Sakurai, T., *Mass Spectrom*, 8:379, 1989.
64. Wahl, J. H.; Gale, D. C.; Smith, R. D., *J. Chromatogr.*, 659:217. 1994.
65. WahI, J. H.; Smith, R. D. *J. Cap. Elec.*, 1:62, 1994.
66. Whitehouse, C. M.; Dreyer, R. N.; Yamashita, M.; Fenn, J. B., *Anal Chem.*, 57:675, 1985.
67. William, S. H., Ed.; "New Methods in Peptide Mapping For The Characterization of Proteins", *CRC Series in Analytical Biotechnology*. ch. 6, 1996.
68. Wu, J. T.; He, L.; Li; M. X.; Parus, S. and Lubman, D. M., *J. Am. Soc. Mass Spectrom.* 1997 (in press).
69. Wu, J. T.; Qian, M. M. G.; Li, M. M. X.; Liu, L. and Lubman, D. M., *Anal. Chem.* 1996, 68, 3388.
70. Yamashita, M., Fenn, J. B., *J. Phys. Chem.*, 88:4451, 1984.
71. Yates, J. R.; Zhou, J.; Griffin, P. R.; Hood, L. E. *Technique in Protein Chemistry II*; Villafranca, J.; Ed.; Academic Press: New York, pp. 477–485, 1990.
72. Yates, J. R.; Speicher, S.; Griffin, P. R. and Hunkapiller, T., *Anal. Biochem.*, 214:397. 1993.

TABLE 1

Tryptic Digests of Horse Cytochrome c in the m/z Range of 500–1000.
Acetyl-GDVEKGKKIFVQKCAQCHTVEK (heme)
GGKHKTGPNLHGLFGRKTGQAPGFTYTDANKNKGITWKEETL
MEYLENPKKYIPGTKMIFAGIKKKTEREDLIAYLKKATNE
(SEQ ID NO: 1) (104 amino acids, MW = 12359.8 Da)

| Peak number | m/z | AA sequence | MW (Da) |
| --- | --- | --- | --- |
| 1 | 589 | Acetyl-GDVEK | 1176 |
| 2 | 965 | EDLIAYLK | 1928 |
| 3 | 736 | TGQAPGFTYTDANK | 1470 |
| 4 | 748 | EETLMEYLENPK | 1494 |
| 5 | 678 | YIPGTK | 677 |
| 6 | 779 | MIFAGIK | 778 |
| 7 | 634 | IFVQK | 633 |
| 8 | 604 | GITWK | 603 |
| 9 | 585 | TGPNLHGLFGR | 1168 |
| 10 | 818 | CAQCHTVEK (heme) | 1634 |

TABLE 2

Tryptic Digests of Horse Heart Myoglobin in
the m/z Range of 500–1000.
GLSDGEWQQVLNVWGKVEADIAGHGQEVLIRLFTGHPETLEK
FDKFKHLKTEAEMKASEDLKKHGTVVLTALGGILKKKGHHEA
ELKPLAQSHATKHKIPIKYLEFISDAIIHVLHS
KHPGDFGADAQGAMTKALELFRNDIAAKYKELGFQG
(SEQ ID NO: 2) (153 amino acids, MW = 16951.5 Da)

| Peak number | m/z | AA sequence | MW (Da) |
|---|---|---|---|
| 1 | 650 | ELGFQG | 649 |
| 2 | 908 | GLSDGEWQQVLNVWGK | 1814 |
| 3 | 631 | NDIAAK | 630 |
| 4 | 804 | VEADIAGHGQEVLIR | 1606 |
| 5 | 708 | TEAEMK | 707 |
| 6 | 748 | ALELFR | 747 |
| 7 | 751 | HPGDFGADAQGAMTK | 1500 |
| 8 | 636 | LFTGHPETLEK | 1270 |
| 9 | 943 | YLEFISDAIIHVLHSK | 1884 |
| 10 | 690 | HGTVVLTALGGILK | 1378 |
| 11 | 943 | YLEFISDAIIHVLHSK | 1884 |

TABLE 3

Measured masses of tryptic digests of horse cytochrome c in
the m/z range of 500–1000.
Acetyl-GDVEKGKKIFVQKCAQCHTVEK (heme)
GGKHKTGPNLHGLFGRKTGQAPGFTYTDANKNKGITWKEETL
MEYLENPKKYIPGTKMIFAGIKKKTEREDLIAYLKKATNE
(SEQ ID NO: 3) (104 amino acids, calculated
average MW 12359.80 Da)

| Peak number | m/z (calculated) | m/z (measured) | Charge state | AA sequence | Error (ppm) |
|---|---|---|---|---|---|
| 1 | 589.283 | 589.282 | +1 | Acetyl-GDVEK | <1.0 |
| 2 | 964.536 | 964.529 | +1 | EDLIAYLK | 7.3 |
| 3 | 735.847 | 735.856 | +2 | TGQAPGFTYTDANK | 12.2 |
| 4 | 748.354 | 748.362 | +2 | EETLMEYLENPK | 10.7 |
| 5 | 678.383 | 678.383 | +1 | YIPGTK | <1.0 |
| 6 | 779.449 | 779.440 | +1 | MIFAGIK | 11.5 |
| 7 | 634.385 | 634.387 | +1 | IFVQK | 3.2 |
| 8 | 604.346 | 604.343 | +1 | GITWK | 5.0 |
| 9 | 584.815 | 584.825 | +2 | TGPNLHGLFGR | 17.1 |
| 10 | 817.822 | 817.825 | +2 | CAQCHTVEK (heme) | 3.7 |

TABLE 4

Measured masses of tryptic digests of horse heart myoglobin in
the m/z range of 500–1000.
GLSDGEWQQVLNVWGKVEADIAGHGQEVLIRLFTGHPETLEKFDKFKHLKTEAEMKA
SEDLKKHGTVVLTALGGILKKKGHHEAELKPLAQSHATKHKIPIKYLEFISDAIIHVLHS
KHPGDFGADAQGAMTKALELFRNDIAAKYKELGFQG (SEQ ID NO: 4) (153 amino
acids, calculated average MW 16951.53 Da)

| Peak number | m/z (calculated) | m/z (measured) | Charge state | AA sequence | Error (ppm) |
|---|---|---|---|---|---|
| 1 | 650.315 | 650.305 | +1 | ELGFQG | 15.4 |
| 2 | 908.455 | 908.457 | +2 | GLSDGEWQQVLNVWGK | 2.2 |
| 3 | 662.336 | 662.335 | +1 | ASEKLK | 1.5 |
| 4 | 631.342 | 631.341 | +1 | NDIAAK | 1.6 |
| 5 | 803.932 | 803.934 | +2 | VEADIAGHGQEVLIR | 2.5 |
| 6 | 708.324 | 708.322 | +1 | TEAEMK | 2.8 |
| 7 | 748.436 | 748.425 | +1 | ALELFR | 14.7 |
| 8 | 751.839 | 751.848 | +2 | HPGDFGADAQGAMTK | 12.0 |
| 9 | 636.336 | 636.340 | +2 | LFTGHPETLEK | 6.3 |
| 10 | 689.925 | 689.931 | +2 | HGTVVLTALGGILK | 8.7 |
| 11 | 943.015 | 943.015 | +2 | YLEFISDAIIHVLHSK | <1.0 |

TABLE 5

Measured masses of the collisionally induced fragments of tryptic digests of cytochrome c in the m/z range of 350–1500 using in-source fragmentation.

| Peak number | AA sequence | Measured Fragments' m/z Error (fragment type, ppm error) |
|---|---|---|
| 1 | Acetyl-GDVEK | 375.226 ($Y''_3$, 4) |
| 2 | EDLIAYLK | 423.268 ($Y''_3$, 17), 494.306 ($Y''_4$, 16), 607.401 ($Y''_5$, 31), 720.486 ($Y''_6$, 28), 835.499 ($Y''_7$, 7) |
| 3 | TGQAPGFTYTDANK | 447.239 ($Y''_4$, 42), 548.283 ($Y''_5$, 27), 711.329 ($Y''_6$, 3), 812.395 ($Y''_7$, 20), 959.461 ($Y''_8$, 14), 1016.463 ($Y''_9$, 6), 1113.531 ($Y''_{10}$, 9), 1184.594 ($Y''_{11}$, 30), 1369.631 ($Y''_{13}$, 6), 1470.709 ([M + H]$^+$, 15) |
| 4 | EETLMEYLENPK | 487.258 ($Y''_4$, 13), 600.337 ($Y''_5$, 2), 763.397 ($Y''_6$, 2), 892.434 ($Y''_7$, 8), 1023.475 ($Y''_8$, 7), 1136.560 ($Y''_9$, 5), 1237.616 ($Y''_{10}$, 2), 1495.649 ([M + H]$^+$, 33) |
| 5 | YIPGTK | 402.238 ($Y''_4$, 7) |
| 6 | MIFAGIK | no fragments detected |
| 7 | IFVQK | 374.251 ($Y''_3$, 29), 521.317 ($Y''_4$, 16) |
| 8 | GITWK | 434.247 ($Y''_3$, 16) |
| 9 | TGPNLHGLFGR | 379.212 ($Y''_3$, 7), 492.306 ($Y''_4$, 26), 549.331 ($Y''_5$, 30), 686.396 ($Y''_6$, 33), 799.472 ($Y''_7$, 18) |
| 10 | CAQCHTVEK \| \| heme | 375.227 ($Y''_3$, 7), 476.271 ($Y''_4$, 2), 613.3421 ($Y''_5$, 18), 716.351 ($Y''_6$, 15), 844.408 ($Y''_7$, 11), 617.202 (heme, 7) |

TABLE 6

Measured masses of tryptic digests of hemoglobin S in the m/z range of 350–1500.

| Peak number | m/z (measured) | m/z (calculated) | Charge state | AA sequence | Error (ppm) |
|---|---|---|---|---|---|
| 1 | 461.275 | 461.273 | +1 | TNVK | 4.3 |
| 2 | 531.288 | 532.289 | +1 | AAWGK | 1.8 |
| 3 | 765.374 | 765.371 | +2 | VGAHAGEYGAEALER | 3.9 |
| 4 | 536.280 | 536.281 | +2 | MFLSFPTTK | 1.8 |
| 5 | 917.440 | 917.450 | +2 | TYFPHFDLSHGSAQVK | 10.8 |
| 6 | 409.731 | 409.724 | +2 | VDPVNFK | 17 |
| 7 | 626.855 | 626.862 | +2 | FLASVSTVLTSK | 11.1 |
| 8 | 461.772 | 461.772 | +2 | VHLTPVEK | <1 |
| 9 | 466.765 | 466.764 | +2 | SAVTALWGK | 2.1 |
| 10 | 657.834 | 657.867 | +2 | VNVDEVGGEALGR | 4.5 |
| 11 | 637.868 | 637.867 | +2 | LLVVYPWTQR | 1.5 |
| 12 | 412.234 | 412.231 | +1 | AHGK | 7.2 |
| 13 | 835.438 | 835.450 | +2 | VLGAFSDGLAHLDNLK | 14.3 |
| 14 | 711.341 | 711.341 | +2 | GTFATLSELH | <1 |
| 15 | 563.784 | 563.786 | +2 | LHVDPENFR | 3.5 |
| 16 | 689.854 | 689.854 | +2 | EFTPPVQAAYQK | <1 |
| 17 | 575.337 | 575.341 | +2 | VVAGVANALAHK | 6.9 |

What is claimed is:

1. A method for chemically analyzing a chemical or biological sample using capillary electrophoresis/electrospray ionization-mass spectrometry, comprising the steps of:
   providing a capillary column having a wall and at least one electrode inside the capillary column, the at least one electrode being attached via an opening in the wall of the capillary column and extending longitudinally within the capillary column;
   providing a mass spectrometer in operable relation to the capillary column;
   applying a voltage potential across the capillary column;
   injecting a mixture containing the chemical or biological sample into the capillary column;
   transporting at least a portion of the mixture to the mass spectrometer; and
   analyzing the portion with the mass spectrometer to identify the composition of the chemical or biological sample in the portion.

2. The method of claim 1, further comprising the step of:
   preconditioning the capillary column with a buffer solution prior to the step of injecting the mixture.

3. The method of claim 1, further comprising the steps of:
   maintaining an inlet pressure at a first pressure level at an inlet end of the capillary column for a first period of time;
   ramping the inlet pressure to a second pressure level once at least a portion of the mixture containing the chemical or biological sample has eluted from the capillary column; and
   maintaining the inlet pressure at the second pressure level for a second period of time.

4. The method of claim 3, wherein the step of ramping the inlet pressure increases the inlet pressure at a rate of constant acceleration.

5. The method of claim 3, wherein the step of ramping the inlet pressure increase the inlet pressure at a variable rate of acceleration.

6. The method of claim 1, further comprising the steps of:
   maintaining an inlet pressure at a first pressure level at an inlet end of the capillary column for a first period of time;
   ramping the inlet pressure to a second pressure level once at least a portion of the mixture containing the chemical or biological sample has eluted from the capillary column;
   maintaining the inlet pressure at the second pressure level for a second period of time;
   and
   ramping the inlet pressure to a third pressure level once the second period of time has elapsed.

7. The method of claim 6, wherein the step of ramping the inlet pressure to the second pressure level or the step of ramping the inlet pressure to the third pressure level increases the inlet pressure at a rate of constant acceleration.

8. The method of claim 6, wherein the step of ramping the pressure to the third pressure level is performed at a higher acceleration rate than the step of ramping the pressure to the second pressure level.

* * * * *

UNITED STATES PATENT AND TRADEMARK OFFICE
CERTIFICATE OF CORRECTION

| | | |
|---|---|---|
| PATENT NO. | : 6,863,790 B1 | Page 1 of 1 |
| APPLICATION NO. | : 09/370781 | |
| DATED | : March 8, 2005 | |
| INVENTOR(S) | : Moini et al. | |

It is certified that error appears in the above-identified patent and that said Letters Patent is hereby corrected as shown below:

In claim 1, column 35, line 6, please delete "wall" and insert --sidewall--.

In claim 1, column 35, line 8, please delete "wall" and insert --sidewall spaced from a terminus--.

In claim 5, column 36, line 7, please delete "increase" and insert --increases--.

Signed and Sealed this

Fifteenth Day of July, 2008

JON W. DUDAS
*Director of the United States Patent and Trademark Office*

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
    (A) LENGTH: 104 amino acids
    (B) TYPE: amino acid
    (C) STRANDEDNESS: <Unknown>
    (D) TOPOLOGY: linear (ix) FEATURE:
    (A) NAME/KEY: Modified-site
    (B) LOCATION:1
    (D) OTHER INFORMATION:/note= "Glycine equals acetyl-glycine"

```
    (ix) FEATURE:
         (A) NAME/KEY: Modified-site
         (B) LOCATION:22
         (D) OTHER INFORMATION:/note= "Lysine is linked to a heme
             group"

(xi) SEQUENCE DESCRIPTION: SEQ ID NO: 1:

Gly Asp Val Glu Lys Gly Lys Lys Ile Phe Val Gln Lys Cys Ala Gln
1               5                   10                  15

Cys His Thr Val Glu Lys Gly Gly Lys His Lys Thr Gly Pro Asn Leu
                20                  25                  30

His Gly Leu Phe Gly Arg Lys Thr Gly Gln Ala Pro Gly Phe Thr Tyr
            35                  40                  45

Thr Asp Ala Asn Lys Asn Lys Gly Ile Thr Trp Lys Glu Glu Thr Leu
50                      55                  60

Met Glu Tyr Leu Glu Asn Pro Lys Lys Tyr Ile Pro Gly Thr Lys Met
65                  70                  75                  80

Ile Phe Ala Gly Ile Lys Lys Lys Thr Glu Arg Glu Asp Leu Ile Ala
                85                  90                  95

Tyr Leu Lys Lys Ala Thr Asn Glu
                100

(2) INFORMATION FOR SEQ ID NO: 2:

(i) SEQUENCE CHARACTERISTICS:
        (A) LENGTH: 153 amino acids
        (B) TYPE: amino acid
        (C) STRANDEDNESS: <Unknown>
        (D) TOPOLOGY: linear (xi) SEQUENCE DESCRIPTION: SEQ ID NO: 2:

Gly Leu Ser Asp Gly Glu Trp Gln Gln Val Leu Asn Val Trp Gly Lys
1               5                   10                  15

Val Glu Ala Asp Ile Ala Gly His Gly Gln Glu Val Leu Ile Arg Leu
                20                  25                  30

Phe Thr Gly His Pro Glu Thr Leu Glu Lys Phe Asp Lys Phe Lys His
            35                  40                  45

Leu Lys Thr Glu Ala Glu Met Lys Ala Ser Glu Asp Leu Lys Lys His
50                      55                  60

Gly Thr Val Val Leu Thr Ala Leu Gly Gly Ile Leu Lys Lys Lys Gly
65                  70                  75                  80

His His Glu Ala Glu Leu Lys Pro Leu Ala Gln Ser His Ala Thr Lys
                85                  90                  95

His Lys Ile Pro Ile Lys Tyr Leu Glu Phe Ile Ser Asp Ala Ile Ile
                100                 105                 110

His Val Leu His Ser Lys His Pro Gly Asp Phe Gly Ala Asp Ala Gln
            115                 120                 125

Gly Ala Met Thr Lys Ala Leu Glu Leu Phe Arg Asn Asp Ile Ala Ala
            130                 135                 140

Lys Tyr Lys Glu Leu Gly Phe Gln Gly
145                 150

(2) INFORMATION FOR SEQ ID NO: 3:

(i) SEQUENCE CHARACTERISTICS:
        (A) LENGTH: 104 amino acids
        (B) TYPE: amino acid
        (C) STRANDEDNESS: <Unknown>
        (D) TOPOLOGY: linear
```

```
    (ix) FEATURE:
         (A) NAME/KEY: Modified-site
         (B) LOCATION:1
         (D) OTHER INFORMATION:/note= "Glycine equals
             acetyl-glycine"

(ix) FEATURE:
         (A) NAME/KEY: Modified-site
         (B) LOCATION:22
         (D) OTHER INFORMATION:/note= "Lysine is linked to a heme
             group"

(xi) SEQUENCE DESCRIPTION: SEQ ID NO: 3:

Gly Asp Val Glu Lys Gly Lys Lys Ile Phe Val Gln Lys Cys Ala Gln
1               5                   10                  15

Cys His Thr Val Glu Lys Gly Gly Lys His Lys Thr Gly Pro Asn Leu
                20                  25                  30

His Gly Leu Phe Gly Arg Lys Thr Gly Gln Ala Pro Gly Phe Thr Tyr
            35                  40                  45

Thr Asp Ala Asn Lys Asn Lys Gly Ile Thr Trp Lys Glu Glu Thr Leu
        50                  55                  60

Met Glu Tyr Leu Glu Asn Pro Lys Lys Tyr Ile Pro Gly Thr Lys Met
65                  70                  75                  80

Ile Phe Ala Gly Ile Lys Lys Lys Thr Glu Arg Glu Asp Leu Ile Ala
                85                  90                  95

Tyr Leu Lys Lys Ala Thr Asn Glu
            100

(2) INFORMATION FOR SEQ ID NO: 4:

(i) SEQUENCE CHARACTERISTICS:
        (A) LENGTH: 153 amino acids
        (B) TYPE: amino acid
        (C) STRANDEDNESS: <Unknown>
        (D) TOPOLOGY: linear (xi) SEQUENCE DESCRIPTION: SEQ ID NO: 4:

Gly Leu Ser Asp Gly Glu Trp Gln Gln Val Leu Asn Val Trp Gly Lys
1               5                   10                  15

Val Glu Ala Asp Ile Ala Gly His Gly Gln Glu Val Leu Ile Arg Leu
                20                  25                  30

Phe Thr Gly His Pro Glu Thr Leu Glu Lys Phe Asp Lys Phe Lys His
            35                  40                  45

Leu Lys Thr Glu Ala Glu Met Lys Ala Ser Glu Asp Leu Lys Lys His
        50                  55                  60

Gly Thr Val Val Leu Thr Ala Leu Gly Gly Ile Leu Lys Lys Lys Gly
65                  70                  75                  80

His His Glu Ala Glu Leu Lys Pro Leu Ala Gln Ser His Ala Thr Lys
                85                  90                  95

His Lys Ile Pro Ile Lys Tyr Leu Glu Phe Ile Ser Asp Ala Ile Ile
            100                 105                 110

His Val Leu His Ser Lys His Pro Gly Asp Phe Gly Ala Asp Ala Gln
        115                 120                 125

Gly Ala Met Thr Lys Ala Leu Glu Leu Phe Arg Asn Asp Ile Ala Ala
130                 135                 140

Lys Tyr Lys Glu Leu Gly Phe Gln Gly
145                 150
```